(12) United States Patent
Goudappel et al.

(10) Patent No.: US 10,834,953 B2
(45) Date of Patent: Nov. 17, 2020

(54) DRY CITRUS FIBERS AND USES THEREOF

(71) Applicant: Cargill, Incorporated, Wayzata, MN (US)

(72) Inventors: Gerrit Jan Wilem Goudappel, Vlaardingen (NL); Hendrikus Theodorus Wilhelmus Maria Van Der Hijden, Vlaardingen (NL); Ivo Kohls, Malchin (DE); Asier Rodriguez, Vilvoorde (BE); Krassimir Petkov Velikov, Vlaardingen (NL); Jacques Andre Christian Mazoyer, Carentan (FR)

(73) Assignee: Cargill, Incorporated, Wayzata, MN (US)

( * ) Notice: Subject to any disclaimer, the term of this patent is extended or adjusted under 35 U.S.C. 154(b) by 165 days.

(21) Appl. No.: 15/748,781

(22) PCT Filed: Jul. 27, 2016

(86) PCT No.: PCT/US2016/044226
§ 371 (c)(1),
(2) Date: Jan. 30, 2018

(87) PCT Pub. No.: WO2017/019752
PCT Pub. Date: Feb. 2, 2017

(65) Prior Publication Data
US 2019/0053528 A1 Feb. 21, 2019

(30) Foreign Application Priority Data
Jul. 30, 2015 (EP) .................................... 15178987

(51) Int. Cl.
*A23L 33/22* (2016.01)
*A23L 2/52* (2006.01)
*C11D 3/382* (2006.01)
*A23P 10/40* (2016.01)
*A23L 19/00* (2016.01)
*A23F 3/16* (2006.01)
*A23L 33/105* (2016.01)
*A61K 36/752* (2006.01)

(52) U.S. Cl.
CPC .............. *A23L 33/22* (2016.08); *A23F 3/163* (2013.01); *A23L 2/52* (2013.01); *A23L 19/07* (2016.08); *A23L 33/105* (2016.08); *A23P 10/40* (2016.08); *A61K 36/752* (2013.01); *C11D 3/382* (2013.01)

(58) Field of Classification Search
CPC ........ A23L 33/22; A23L 19/07; A23L 33/105; A23L 2/52; A23P 10/40; A23F 3/163
USPC .......................... 426/616, 429, 464, 518, 548
See application file for complete search history.

(56) References Cited

U.S. PATENT DOCUMENTS

2013/0131012 A1* 5/2013 Gusek et al.

FOREIGN PATENT DOCUMENTS

| WO | 9427451 A1 | 12/1994 |
|---|---|---|
| WO | 2012016190 A1 | 2/2012 |

(Continued)

*Primary Examiner* — Helen F Heggestad
(74) *Attorney, Agent, or Firm* — Schwegman Lundberg & Woessner, P.A.

(57) ABSTRACT

The invention relates to citrus fibers in dry form having a storage modulus (G') of at least 50 Pa, said G' being measured on an aqueous medium containing an amount of 2 wt % citrus fibers dispersed therein under a low-shear stirring of less than 10000 rpm.

13 Claims, 1 Drawing Sheet

(56) References Cited

FOREIGN PATENT DOCUMENTS

| WO | 2012016201 A2 | 2/2012 |
|---|---|---|
| WO | 2013109721 A2 | 7/2013 |

* cited by examiner

DRY CITRUS FIBERS AND USES THEREOF

CROSS REFERENCE TO RELATED APPLICATIONS

This application is a national phase application of PCT/US16/044226, filed 27 Jul. 2016, entitled DRY CITRUS FIBERS AND USES THEREOF, which claims the benefit of priority to European Application No. 15178987.2 filed 30 Jul. 2015, entitled DRY CITRUS FIBERS AND USES THEREOF, which are hereby incorporated by reference in their entirety.

FIELD OF INVENTION

The invention relates to citrus fibers and citrus fibers based composition in dry form and in particular to such fibers and compositions which are readily dispersible. The invention further relates to a method for manufacturing said fibers and compositions and their uses.

BACKGROUND

Citrus fibers are known to have many interesting properties making them suitable for use in a variety of products for human and animal consumption. Citrus fibers have been successfully employed, mainly as texturizing additives, in food and feed products and beverages, but also in personal care, pharmaceutical and detergent products. The use of citrus fibers in dry form (hereinafter "dry citrus fibers") in the manufacturing of the above products is advantageous due to the fibers' longer shelf life and reduced costs of shipping from a fiber production plant or storage site to a processing facility.

Dry citrus fibers and compositions containing thereof are for example known from WO 2006/033697, WO 2012/016190, and WO 2013/109721. When carefully dried, these known citrus fibers may retain an optimum free surface area available for binding water upon rehydration and dispersion, which in turn provides said fibers with thickening capabilities, good stability, and the capacity to create optimum textures. Using various techniques such as the one disclosed in WO 2012/016201, the properties of the dry citrus fibers can be further tailored to provide optimum functionalities.

It is however difficult to prepare dry citrus fibers without affecting their dispersibility in aqueous media. A method of enhancing the dispersibility of dry citrus fibers in an aqueous medium is to functionalize or derivatize the fibers, i.e. grafting various chemical moieties on the surface of the fibers. U.S. Pat. No. 5,964,983 discloses dry fibres, e.g. citrus fibers, functionalized with acidic polysaccharides retained on their surface. These fibers however, can only be dispersed in water with a high-shear mixing device of the ULTRA TURRAX type and cannot be thus considered readily dispersible.

Another method known to provide dry, dispersible fibers, involves drying the fibers in the presence of additives. U.S. Pat. Nos. 6,485,767 and 6,306,207 disclose dry compositions containing up to 20 wt % of a polyhydroxylated compound and dry fibers. Although citrus fibers were mentioned as being a suitable example, no experimental data using such fibers was reported therein. According to the experimental part of these publications, somewhat dry fibers (i.e., fibers having a dry substance content of about 77 wt % and about 23 wt % moisture) extracted from sugar beet pulp were readily dispersible in water using only vigorous stirring (500 rpm). However, the properties of these fibers can be further optimized, in particular their moisture content and/or viscoelastic properties.

It was also observed that known dry compositions containing citrus fibers and additives may have undesirable characteristics such as stickiness, which in turn may cause problems during a subsequent processing thereof. Also, the rheological behavior and viscoelastic stability of such compositions are less than optimum with large variations in G' being observed when changing the nature and/or varying the amounts of the compositions' constituents.

Accordingly, there is an unmet need in the industry for citrus fibers in dry form used as such or in compositions, which can be readily dispersed in an aqueous medium, and which upon dispersion provide said medium with an optimum rheological behavior. More in particular, there is a need for dry citrus fibers used as such or in compositions, which when dispersed in an aqueous medium, provide the aqueous medium with optimum G' values and/or an optimum viscoelastic stability.

SUMMARY OF INVENTION

A primary object of this invention may thus be to provide dry citrus fibers that can be readily dispersed under low-shear stirring in an aqueous medium to form a dispersion having optimum rheological properties.

The foregoing and other objects of this invention are met by providing citrus fibers in dry form having a storage modulus (G') of at least 50 Pa, said G' being measured on an aqueous medium containing an amount of 2 wt % citrus fibers dispersed therein under a low-shear stirring of less than 10000 rpm.

DETAILED DESCRIPTION

Figure 1:
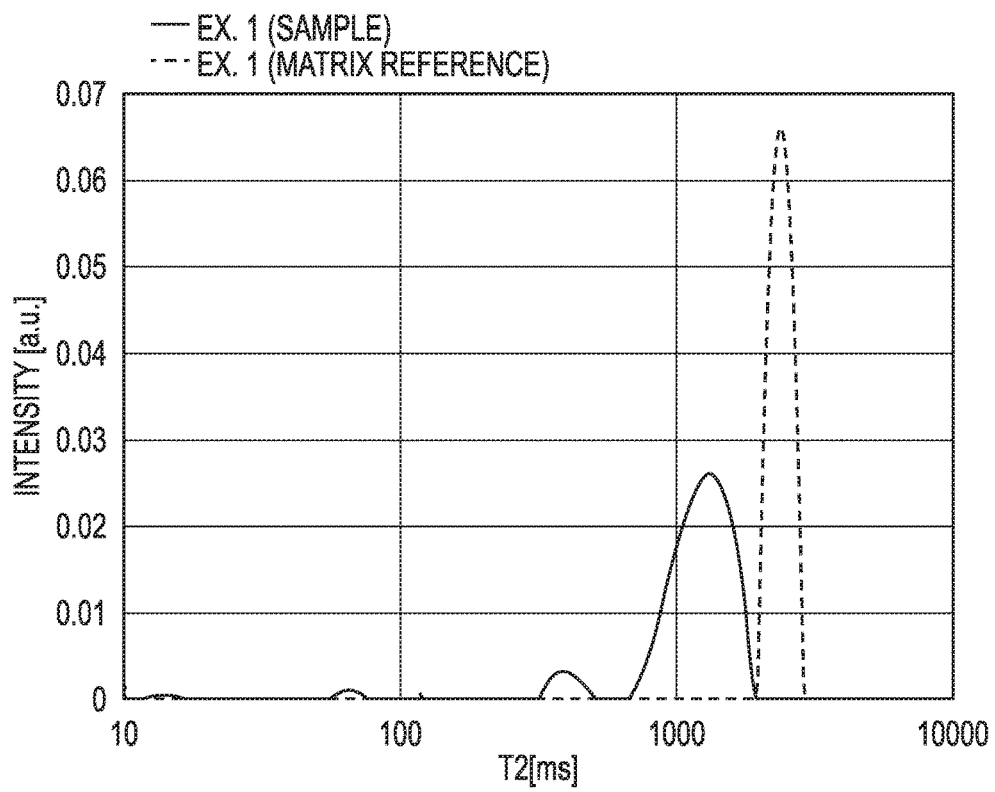
FIGS. 1 and 2 show NMR $T_2$ distribution curves characteristic to the fibers of the invention upon their dispersal under specific conditions as detailed herein.

Any feature of a particular embodiment of the present invention may be utilized in any other embodiment of the invention. The word "comprising" is intended to mean "including" but not necessarily "consisting of" or "composed of". In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the examples and comparative experiments, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated. For the purpose of the invention ambient (or room) temperature is defined as a temperature of about 20 degrees Celsius.

In a first aspect, the present invention provides citrus fibers in dry form having a storage modulus (G') of at least 50 Pa, said G' being measured on an aqueous medium containing an amount of 2 wt % citrus fibers dispersed therein under a low-shear stirring of less than 10000 rpm.

The storage modulus G' is commonly used in the food industry to analyze the rheological properties of dispersions and in particular fiber-based dispersions. In the art, by fiber-based dispersion is understood fibers or compositions containing thereof dispersed in an aqueous medium. G' is a measure of a deformation energy stored in the dispersion during the application of shear forces and provides an excellent indication of the dispersion's viscoelastic behavior. Here, G' is measured on an aqueous medium containing an amount of 2 wt % of citrus fibers, i.e. relative to the total weight of the aqueous medium. It is highly desirable to achieve dispersions having G' values as high as possible at concentrations of fibers as low as possible when the fibers are dispersed under low-shear in the aqueous medium.

The present inventors noticed that the citrus fibers of the invention were able to meet the above requirements and hence, these novel fibers may impart food, feed, pharma or personal care formulations containing thereof with optimum rheological properties. The novel citrus fibers have also an improved dispersibility in that they are readily dispersible in the aqueous medium. Moreover, since said citrus fibers may be used at lower concentrations to achieve increased G' values, food, feed and other manufacturers may have increased design freedom for their respective formulations, in that they may be able to add or remove constituents while maintaining optimum viscoelastic properties thereof.

As used herein, "dispersibility" means that upon dispersion in an aqueous medium, e.g. water, the dry fibers have the capacity to largely regain their initial functionality, wherein by initial functionality is herein understood the functionality of the fibers before being dehydrated and/or dried. Properties defining the initial functionality may include the fibers' swelling capacity, viscoelasticity, water-binding capacity and stabilization power.

The term "readily dispersible" as used herein means that it is not necessary to use high-shear means, e.g. high-shear mixers or homogenizers, to disperse the fibers in an aqueous medium such as water in order to obtain a useful viscosity; but rather that the dispersion of the fibers can be accomplished with low-shear stirring equipment, such as for example, magnetic stirrers or mechanical stirrers, e.g. an IKA® Eurostar mechanical stirrer equipped with an R1342 4-bladed propeller stirrer or a Silverson L4RT overhead batch mixer equipped with an Emulsor Screen (e.g. with round holes of about 1 mm diameter).

The term "aqueous medium" as used herein means a liquid medium which contains water, suitable non-limiting example thereof including pure water, a water solution and a water suspension.

The G' of the citrus fibers of the invention is at least 50 Pa. Preferably, said G' is at least 75 Pa, more preferably at least 100 Pa, even more preferably at least 125 Pa, yet even more preferably at least 150 Pa, most preferably at least 170 Pa.

The inventors surprisingly observed that the citrus fibers of the invention manifest the high G' values upon being dispersed in an aqueous medium under low shear, i.e. stirring with less than 10000 rpm. This is even more surprising since said high G' values were achieved at the low fiber concentrations, e.g. of 2 wt %. The aqueous medium preferably contains water in an amount of at least 75 wt %, more preferably at least 85 wt %, most preferably at least 95 wt %, relative to the total amount of the medium. Preferably, the stirring used to achieve the dispersion of the fibers of the invention in the aqueous medium is at most 8000 rpm, more preferably at most 5000 rpm, most preferably at most 3000 rpm.

The citrus fibers of the invention are in dry form, which is herein understood as containing an amount of liquid, e.g. water and/or organic solvent, of less than 20 wt % relative to the total weight of the fibers. Preferably said fibers contain an amount of water (i.e. moisture content) of at most 12 wt %, more preferably at most 10 wt %, or most preferably at most 8 wt %. Such dry fibers may be more economical to transport and store while being readily dispersible in the aqueous medium.

The fibers of the invention are citrus fibers. The term "fiber" as used herein, refers to an elongated object comprising microfibrils of cellulose, the fiber having a length (major axis) and a width (minor axis) and having length to width ratio of at least 5, more preferably at least 10, or most preferably at least 15, as observed and measured by a high-resolution scanning electron microscope ("SEM"). The length of the citrus fibers is preferably at least 0.5 μm, more preferably at least 1 μm. The width of the citrus fibers is preferably at most 100 nm, more preferably at most 50 nm, most preferably at most 15 nm.

Citrus fibers are fibers contained by and obtained from the fruits of the citrus family. The citrus family is a large and diverse family of flowering plants. The citrus fruit is considered to be a specialized type of berry, characterized by a leathery peel and a fleshy interior containing multiple sections filled with juice filled sacs. Common varieties of the citrus fruit include oranges, sweet oranges, clementines, kumquats, tangerines, tangelos, satsumas, mandarins, grapefruits, citrons, pomelos, lemons, rough lemons, limes and leech limes. The citrus fruit may be early-season, mid-season or late-season citrus fruit. Citrus fruits also contain pectin, common in fruits, but found in particularly high concentrations in the citrus fruits. Pectin is a gel-forming polysaccharide with a complex structure. It is essentially made of partly methoxylated galacturonic acid, rhamnose with side chains containing arabinose and galactose, which are linked through a glycosidic linkage. The pectin content of the citrus fruit may vary based on season, where ripe fruit may contain less pectin than unripe fruit.

Citrus fiber is to be distinguished from citrus pulp, which are whole juice sacs and are sometimes referred to as citrus vesicles, coarse pulp, floaters, citrus cells, floating pulp, juice sacs, or pulp. Citrus fiber is also to be distinguished from citrus rag, which is a material containing segment membrane and core of the citrus fruit.

The citrus fibers are typically obtained from a source of citrus fibers, e.g. citrus peel, citrus pulp, citrus rag or combinations thereof. Moreover, the citrus fibers may contain the components of the primary cell walls of the citrus fruit such as cellulose, pectin and hemicelluloses and may also contain proteins.

Preferably, the citrus fibers of the invention did not undergo any substantial chemical modification, i.e. said fibers were not subjected to chemical modification processes such as esterification, derivatisation or enzymatic modification and combinations thereof.

Preferably, the citrus fibers in accordance with the invention have a crystallinity of at least 10%, more preferably at least 20%, most preferably at least 30% as measured on a dried (less than 20 wt % water content relative to the content of fibers) sample by X-ray diffraction method (Siegel method). Preferably, the crystallinity of said fibers is between 10% and 60%.

The inventors surprisingly found that suitably prepared citrus fibers in dry form can be readily dispersed in an aqueous medium by applying relatively low levels of shear compared to conventional dry citrus fibers. Without wishing to be bound by theory, it is believed that the excellent dispersion properties of the citrus fibres are related to the structure that is imparted on them in the dry form. It was further surprisingly found by the present inventors that this structure can suitably be characterized by a standardized shear storage modulus (G*) that is determined for a standardized dispersion of such citrus fibers.

Consequently, according to a second aspect, the present invention provides citrus fibers, in dry form having a G* of at least 50 Pa, wherein G* is measured by:
a. providing the fibers in a particulate form wherein the particles can pass a 500 tim sieve by milling the citrus fiber material using a Waring 8010EG laboratory blender equipped with an SS110 Pulverizer Stainless Steel Container using its low speed setting (18000 rpm) for 4 plus or minus 1 seconds; sieving the milled material using an AS200 digital shaker from Retsch GmbH Germany with a sieve set of 10 mm, 500 μm, 250 μm and 50 μm sieves, whilst shaking for 1 minute at an amplitude setting of 60; remilling and resieving the particles larger than 500 μm until they passed the 500 μm sieve and combining the sieved fractions;
b. dispersing an amount of the fibers in particulate form so as to obtain 300 grams of an aqueous dispersion comprising 2 wt % of dry citrus fiber by weight of the dispersion, wherein the dispersion is buffered at pH 7.0, and whereby the fibers are dispersed using a Silverson overhead mixer equipped with an Emulsor screen having round holes of 1 mm diameter at 3000 rpm for 120 seconds; and
c. determining G* of the resultant dispersion using a parallel plate rheometer.

Step a. of the above protocol for the determination of G* serves to facilitate efficient dispersion during step b. The citrus fiber in dry form may come at a variety of particle sizes. Therefore, step a. includes milling of the citrus fiber so as to obtain the fibers in the specified particulate form. Suitable milling is provided by dry milling using a laboratory-scale Waring blender. The buffered dispersion of step b. may be prepared using any suitable buffer system. Preferably, a phosphate-based buffer is used. In step c, the Silverson overhead mixer preferably is an L4RT overhead mixer. G* is measured using any suitable parallel plate rheometer, for example an ARG2 rheometer of TA Instruments. G* is preferably measured at a strain level of 0.1%. A preferred way of establishing the G* is by following the protocol in the way described below. The above protocol and the Examples provide methods of measuring the G*. However, the G* may also be determined by a different protocol, as long as that protocol would lead to the same physical result, i.e. it would yield the same G* for a particular dry citrus fiber preparation as the above protocol.

The citrus fibers in dry form according to the second aspect of the invention preferably have a G* of at least 100 Pa, more preferably at least 150 Pa, even more preferably at least 200 Pa, still more preferably at least 250 Pa, and yet more preferably at least 300 Pa and even more preferably at least 350 Pa. The citrus fibers in dry form preferably have a G* of up to 10000 Pa, and more preferably of up to 1000 Pa. Thus it is particularly preferred that the citrus fibers in dry form have a G* of between 50 Pa and 10000 Pa, more preferably between 300 Pa and 1000 Pa.

In a third aspect, the present invention provides a composition of matter in dry form comprising citrus fibers and an additive distributed between said fibers, said composition having a storage modulus (G') of at least 100 Pa, said G' being measured on an aqueous medium obtained by dispersing therein an amount of said composition under a low shear stirring of less than 10000 rpm to obtain a citrus fibers' concentration of 2 wt % relative to the total weight of the aqueous medium. Preferably, G' is at least 150 Pa, more preferably at least 170 Pa, even more preferably at least 190 Pa, yet even more preferably at least 250 Pa, yet even more preferably at least 300 Pa, most preferably at least 350 Pa when said composition is dispersed under a low shear stirring of less than 5000 rpm, more preferably less than 3000 rpm. Preferably, G' is at least 375 Pa, more preferably at least 425 Pa, even more preferably at least 475 Pa, yet even more preferably at least 550 Pa, yet even more preferably at least 600 Pa, most preferably at least 650 Pa when said composition is dispersed under a low shear stirring of between 6000 and 10000 rpm, more preferably between 7500 and 8500 rpm.

The composition of the invention, hereinafter the inventive composition, is in dry form, which is herein understood that the composition contains an amount of liquid, e.g. water and/or organic solvent, of less than 20 wt % relative to the total weight of said composition. Preferably the composition contains an amount of water of at most 12 wt %, more preferably at most 10 wt %, or most preferably at most 8 wt %. Such a dry composition may be more economical to transport and store.

The inventive composition comprises an additive distributed between the citrus fibers. By the term "additive distributed between the citrus fibers" is herein understood that said additive is distributed inside a volume defined by the totality of fibers and preferably also between the microfibrils forming the fibers. Preferably, the citrus fibers used in the inventive composition are the citrus fibers of the invention.

Preferably, the inventive composition contains the additive in an amount of at least 5 wt % relative to the weight of the anhydrous citrus fibers contained by said composition, more preferably of at least 10 wt %, even more preferably of at least 20 wt %, or most preferably of at least 30 wt %. The weight of the anhydrous fibers in the composition is the weight of the fibers obtained by drying 10 grams of the composition without the additive at 105° C. under normal atmosphere until constant weight is obtained. The same determination can be carried out in the presence of the additive; however, in this case the amount of additive in the sample has to be subtracted therefrom. The upper limit for the additive amount in the inventive composition can be kept within large variances since it was observed that the citrus fibers contained by said composition may have the ability to optimally include said additive. A preferred upper limit for the additive amount is at most 1000 wt % relative to the weight of the fibers in said composition, more preferably at most 750 wt %, or most preferably at most 500 wt %.

Preferably, the inventive composition has an additive: fiber (A:F) ratio of between 0.01:1.0 and 10.0:1.0 by weight, more preferably between 0.1:1.0 and 9.0:1.0 by weight, most preferably between 0.4:1.0 and 8.0:1.0 by weight. In a first embodiment, the A:F ratio is between 0.01:1.0 and 3.8:1.0, more preferably between 0.05:1.0 and 3.4:1.0, most preferably between 0.10:1.0 and 3.0:1.0. In a second embodiment, the A:F ratio is between 4.0:1.0 and 10.0:1.0, more preferably between 4.5:1.0 and 9.0:1.0, most preferably between 5.0:1.0 and 8.0:1.0. The inventors observed that the inventive composition has stable rheological properties in that when varying the A:F ratio of the composition, the G' varies with a standard deviation (STDEV) of at most 50% of a maximum (MAX), wherein MAX is the maximum measured value of the G'.

For compositions comprising additives and fibers. G' may depend on the amount and nature of the fibers but also on the A:F ratio. In other words, a composition with a specific A:F ratio has a specific G' and by changing said ratio, G' changes also. The amount with which G' changes with the A:F ratio, e.g. as expressed in terms of the standard deviation (STDEV), may give an indication of the dispersibility and the rheological (or viscoelastic) stability of the composition.

The inventors observed that while changing the A:F ratio of the inventive composition, G' may experience a maximum (MAX); and that the deviation expressed as STDEV of G' from MAX for various A:F ratios may also give an indication on the dispersibility and the rheological stability of the composition. They observed that an increased deviation of STDEV from MAX may deleteriously influence the processability of the composition as processing steps with starkly different sets of parameters may be required for each A:F ratio in order to achieve an optimal processing thereof. The inventors also observed that various characteristics of the composition such as shelf stability and sensory perception, including texture and mouthfeel may also be negatively influenced by an increased deviation of STDEV from MAX.

The inventors observed that in the known compositions, additives were not efficiently mixed with said fibers, which may result in a less optimal distribution of the additive between the fibers. This may be reflected by the compositions' less optimal rheological behaviour, e.g. large variations of the compositions' G' with the A:F ratio and in particular large deviations of STDEV from MAX.

For the composition of the invention the STDEV characteristic to the G' variations is at most 50% of the MAX. Preferably, the STDEV is at most 40% of said MAX, more preferably at most 30% of said MAX, even more preferably at most 20% of said MAX, most preferably at most 16% of said MAX. The inventive composition may also be considered readily dispersible. Moreover, the inventors observed that when the A:F ratio is varied, the obtained G' values are closely grouped around the MAX; hence the inventive composition may have a viscoelastic behavior which is less dependent on the concentration and/or nature of added constituents than known citrus fiber-based compositions and may thus offer increased design freedom for products whose rheological or other properties are modified with the help of these citrus fibers.

The additive used in the inventive composition, is preferably chosen from carbohydrates and polyols. Carbohydrates include also derivatives thereof. Preferred carbohydrates are linear or cyclic monosaccharides, oligosaccharides, polysaccharides and fatty derivatives thereof. Examples of fatty derivatives may include sucroesters or fatty acid sucroesters, carbohydrate alcohols and mixtures thereof. Non-limiting examples of monosaccharides include fructose, mannose, galactose, glucose, talose, gulose, allose, altrose, idose, arabinose, xylose, lyxose and ribose. Non-limiting examples of oligosaccharides include sucrose, maltose and lactose. Non-limiting examples of polysaccharides include nonionic polysaccharides, e.g. galactomannans, such as guar gum, carob gum, starch and its nonionic derivatives, and nonionic cellulose derivatives; but also anionic polysaccharides such as xanthan gum, succinoglycans, carrageenans and alginates. Preferred examples of polyols include without limitation glycerol, pentaerythritol, propylene glycol, ethylene glycol and/or polyvinyl alcohols. The additives enumerated above can be used alone or in mixtures or blends of two or more additives.

In a preferred embodiment, the additive is a hydrophilic additive, suitable examples including dextrins; water-soluble sugars such as glucose, fructose, sucrose, lactose, isomerized sugar, xylose, trehalose, coupling sugar, paratinose, sorbose, reduced starch-saccharified gluten, maltose, lactulose, fructo-oligosaccharide, galacto-oligosaccharide; hydrophilic starches and sugar alcohols such as xylitol, maltitol, mannitol and sorbitol but also combinations thereof.

In another preferred embodiment, the additive is a starch. The starch used in this invention may be any starch derived from any native source. A native starch as used herein, is one as it is found in nature. Also suitable are starches derived from a plant obtained by any known breeding techniques. Typical sources for the starches are cereals, tubers and roots, legumes and fruits. The native source can be any variety, including without limitation, corn, potato, sweet potato, barley, wheat, rice, sago, amaranth, tapioca (cassava), arrowroot, canna, pea, banana, oat, rye, triticale, and sorghum, as well as low amylose (waxy) and high amylose varieties thereof. Low amylose or waxy varieties is intended to mean a starch containing at most 10% amylose by weight, preferably at most 5%, more preferably at most 2% and most preferably at most 1% amylose by weight of the starch. High amylose varieties is intended to mean a starch which contains at least 30% amylose, preferably at least 50% amylose, more preferably at least 70% amylose, even more preferably at least 80% amylose, and most preferably at least 90% amylose, all by weight of the starch. The starch may be physically treated by any method known in the art to mechanically alter the starch, such as by shearing or by changing the granular or crystalline nature of the starch, and as used herein is intended to include conversion and pregelatinization. Methods of physical treatment known in the art include ball-milling, homogenization, high shear blending, high shear cooking such as jet cooking or in a homogenizer, drum drying, spray-drying, spray cooking, chilsonation, roll-milling and extrusion, and thermal treatments of low (e.g. at most 2 wt %) and high (above 2 wt %) moisture containing starch. The starch may be also chemically modified by treatment with any reagent or combination of reagents known in the art. Chemical modifications are intended to include crosslinking, acetylation, organic esterification, organic etherification, hydroxyalkylation (including hydroxypropylation and hydroxyethylation), phosphorylation, inorganic esterification, ionic (cationic, anionic, nonionic, and zwitterionic) modification, succination and substituted succination of polysaccharides. Also included are oxidation and bleaching. Such modifications are known in the art, for example in Modified starches: Properties and Uses. Ed. Wurzburg, CRC Press, Inc., Florida (1986).

In another preferred embodiment, the additive is a blend containing a first additive and a second additive, the first additive being a starch and the second additive being a carbohydrate, a derivatives thereof or a polyol, wherein the second additive is different than the first additive. Preferably, the starch is chosen from the group of starches containing a native starch, a thermally treated starch, a chemically modified starch and combinations thereof. Preferably, the second additive is chosen from the group consisting of glucose, sucrose, glycerol and sorbitol.

Most preferred additives for use in the inventive composition are glucose, sucrose, glycerol and sorbitol.

The inventors surprisingly found that a suitably prepared composition of matter in dry form, comprising citrus fibers and an additive distributed between said fibers can be readily dispersed in an aqueous medium by applying relatively low levels of shear compared to conventional dry citrus fibers. It was further surprisingly found by the present inventors that this structure can suitably be characterised by a standardized modulus (G*) that is determined for a standardized dispersion of the composition of matter. Consequently, according to a fourth aspect, the present invention provides a composition of matter in dry form comprising citrus fibers and an additive distributed between said fibers, said composition having a G* of at least 150 Pa, wherein G* is measured by
a. providing the composition in a particulate form wherein the particles can pass a 500 µm sieve by milling the citrus fiber material using a Waring 8010EG laboratory blender equipped with an SS110 Pulverizer Stainless Steel Container using its low speed setting (18000 rpm) for 4 plus or minus 1 seconds; sieving the milled material using an AS200 digital shaker from Retsch GmbH Germany with a sieve set of 10 mm, 500 µm, 2501 µm and 50 µm sieves, whilst shaking for 1 minute at an amplitude setting of 60; remilling and resieving the particles larger than 500 µm until they passed the 500 µm sieve and combining the sieved fractions;
b. dispersing an amount of the composition in particulate form so as to obtain 300 grams of an aqueous dispersion comprising 2 wt % of dry citrus fiber by weight of the dispersion, wherein the dispersion is buffered at pH 7.0, and whereby the fibers are dispersed using a Silverson overhead mixer equipped with an Emulsor screen having round holes of 1 mm diameter at 3000 rpm for 120 seconds; and
c. determining G* of the resultant dispersion using a parallel plate rheometer.

Step a. of the above protocol for the determination of G* serves to facilitate efficient dispersion during step b. The composition of matter in dry form may come at a variety of particle sizes. Therefore, step a. includes milling of the composition so as to obtain the fibers in the specified particulate form. Suitable milling is provided by dry milling using a laboratory-scale Waring blender. The buffered dispersion of step b. may be prepared using any suitable buffer system. Preferably, a phosphate-based buffer is used. In step c, the Silverson overhead mixer preferably is an L4RT overhead mixer. G* is measured using any suitable parallel plate rheometer, for example an ARG2 rheometer of TA Instruments. G* is preferably measured at a strain level of 0.1%. A preferred way of establishing the G* is by following the protocol in the way described below. The above protocol and the Examples provide methods of measuring the G*. However, the G* may also be determined by a different protocol, as long as that protocol would lead to the same physical result, i.e. it would yield the same G* for a particular dry citrus fiber preparation as the above protocol.

The composition of matter in dry form according to the fourth aspect of the invention preferably has a G* of at least 200 Pa, more preferably at least 250 Pa, even more preferably at least 300 Pa and still more preferably at least 350 Pa. The composition of matter in dry form preferably has a G* of up to 10000 Pa, and more preferably of up to 1000 Pa. Thus it is particularly preferred that the composition of matter in dry form has a G* of between 150 Pa and 10000 Pa, more preferably between 300 Pa and 1000 Pa.

The preferences and examples regarding the citrus fiber, the type and amount of additive in the composition of matter according to this fourth aspect of the invention are as presented hereinabove for the composition of matter in dry form comprising citrus fibers and an additive distributed between said fibers according to the present invention. It is particularly preferred that the additive is sucrose and that the ratio A:F of additive to citrus fiber is 0.10 to 1.0 and 3.0 to 1.0 by weight.

In a fifth aspect, the present invention provides cellulose fibers in dry form having a transverse relaxation factor ("$R_2$*") as measured by nuclear magnetic resonance ("NMR") of at least 0.65. The preferred cellulose fibers are citrus fibers. Preferably, the $R_2$* of said dry cellulose fibers is at least 0.70, more preferably at least 0.80, even more preferably at least 0.90, yet even more preferably at least 1.10, and most preferably at least 1.20. Preferably, the moisture content of the dry cellulose fibers is at most 20 wt % relative to the total mass of fibers, more preferably at most 12 wt %, even more preferably at most 10 wt %, most preferably at most 8 wt %. To inventors' knowledge, cellulose fibers and in particular citrus fibers dried to a moisture content below the above mentioned amounts and having the $R_2$* in accordance with the invention were never manufactured hitherto.

The inventors surprisingly observed that $R_2$* may be used to characterize and describe dry cellulose fibers and in particular dry citrus fibers. Without being bound to any theory, it is believed that $R_2$* may provide an indication of the magnitude of the available surface area of the fibers. A higher $R_2$* value thus signifies a larger available surface area of a fiber, which in turn may indicate an increased texturizing capacity of the fibers, i.e. the ability of the fibers to form and/or stabilize textures. It was observed that $R_2$* values, such as those characteristic for the fibers of the invention, were never achieved hitherto, as the publicly reported values and the measured values of any commercial products existent so far are well below 0.65. It is thus believed that the known dry cellulose fibers and in particular the known dry citrus fibers have a less than optimum texturizing capacity.

The inventors surprisingly found that suitably prepared citrus fibers in dry form can be readily dispersed in an aqueous medium by applying relatively low levels of shear compared to conventional dry citrus fibers. Likewise, it was surprisingly found that redispersion of a suitably prepared composition of matter in dry form comprising citrus fibers and an additive distributed between said fibers can be dispersed even more readily. Without wishing to be bound by theory, it is believed that the excellent dispersion properties of said citrus fibers or said composition in dry form are related to the structure that is imparted on them in the dry form. It was further surprisingly found by the present inventors that this structure can suitably be characterized by a Fiber Availability Parameter (FAP). This finding applies to both the citrus fibers in dry form and to the composition of matter in dry form. The FAP is measured using a technique based on NMR. Therefore, according to a sixth aspect, the invention provides citrus fibers in dry form having a FAP of at least 0.35 Hz. Similarly, according to a seventh aspect, the invention provides a composition of matter in dry form comprising citrus fibers and an additive distributed between said fibers having a FAP of at least 0.70 Hz.

The FAP is determined in essentially the same way for both the citrus fibers according to the sixth aspect and the composition of matter in dry form according to the seventh aspect of the invention. Therefore, the term "citrus fiber material" is herein understood to refer to either the citrus fibers in dry form according to the sixth aspect or the composition of matter in dry form comprising citrus fibers and an additive distributed between said fibers according to the seventh aspect of the invention, as the case may be. The FAP provides a measure for the internal configuration of the citrus fiber material and the extent to which the fibers are available for redispersion at low shear levels as a result of that configuration. The FAP is based on the NMR method performed on a standardized sample comprising the citrus fiber material in dispersed form. The FAP of the citrus fiber material is established by the following protocol. The protocol to establish FAP includes three parts: sample preparation, NMR measurement to collect Carr-Purcell-Meiboom-Gill (CPMG) relaxation decay data, and data analysis to calculate the FAP value. Thus, the protocol includes the sample preparation steps of:

a. providing the citrus fiber material in a particulate form wherein the particles can pass a 500 μm sieve, by milling the citrus fibre material using a Waring 8010EG laboratory blender equipped with an SS110 Pulverizer Stainless Steel Container using its low speed setting (18000 rpm) for 4 plus or minus 1 seconds; sieving the milled material using an AS200 digital shaker from Retsch GmbH Germany with a sieve set of 10 mm, 500 μm, 250 μm and 50 μm sieves, whilst shaking for 1 minute at an amplitude setting of 60; remilling and resieving the particles larger than 500 m until they passed the 500 μm sieve and combining the sieved fractions;

b. using the citrus fiber material to prepare 300 grams of a concentration-standardized sample in the form of a dispersion at room temperature, wherein the concentration-standardized sample comprises the fibers contained in the citrus fiber material at a concentration of 0.50 wt-% with respect to the weight of the standardized sample; by first combining the citrus fiber material with water to gain a total weight of 250 grams, optionally adding a preservative, adjusting the concentration of the sample to a pH of 3.6±0.1 using aqueous hydrochloric acid and adjusting the volume of the resulting mixture to a total of 300 grams by adding water;

c. evenly distributing the fibers inside the concentration-standardized sample volume by agitating the sample using a Silverson overhead mixer equipped with an Emulsor screen having round holes of 1 mm diameter at 1500 rpm for 120 seconds;

d. adjusting the pH of the concentration-standardized sample to 3.3±0.1;

e. transferring an aliquot of the concentration- and pH-standardized sample to a flat-bottom NMR tube of 10 mm diameter, ensuring a fill height such that upon placement of the sample in the NMR spectrometer of step h, the fill height is within the region where the RF field of the coil of the NMR spectrometer is homogeneous.

Step a. of the above protocol for the determination of the FAP serves to facilitate efficient dispersion during step b. The citrus fiber material may come at a variety of suitable particle sizes. Therefore, step a. includes milling of the citrus fiber material so as to obtain the material in the specified particulate form. Suitable milling is provided by dry milling using a laboratory-scale Waring blender. The sample is preferably kept or made free from larger particulate material, including for instance fragments of whole or multiple cells and other non-homogenized material. The distributing step c is intended to provide an even distribution of the fibers over the sample volume, whilst having a controlled effect on the availability of the fibers for dispersion. In step d. the pH is suitably standardized with the aid of hydrochloric acid. The optimal fill height in step e may depend on the type of NMR spectrometer used, as known by the skilled person. It will typically be about 1 cm. In the further steps of the protocol, the concentration- and pH-standardized sample will be referred to as the standardized sample.

The data analysis requires comparison of a $T_2$ distribution curve (see below) of the standardized sample with a matrix reference sample, which should preferably be essentially free from cellulose fibers. Therefore, the protocol also includes the step of:

f. preparing a matrix reference sample by centrifuging an aliquot of the standardized sample in a 2 ml Eppendorf cup at a relative centrifugation force of 15000 for 10 minutes and transferring the supernatant to a flat-bottom NMR tube of 10 mm diameter, ensuring a fill height such that upon placement of the sample in the NMR spectrometer of step h, the fill height is within the region where the RF field of the coil of the NMR spectrometer is homogeneous.

Subsequently, to collect and analyze the data, the protocol includes the steps of g. equilibrating the NMR tubes at a temperature of 20° C.;

h. recording relaxation decay data for the standardized sample at 20° C. on an NMR spectrometer operating at a proton resonance frequency of 20 MHz, using a CPMG $T_2$ relaxation pulse sequence, with a 180° pulse spacing of 200 microseconds, and a recycle delay time of 30 seconds;

i. recording relaxation decay data for the matrix reference sample under the same conditions as in step h;

j. performing inverse Laplace transformation to the obtained decay data for both the standardized sample and the matrix reference sample, requiring $T_2$ to be in the range of 0.01 to 10 seconds;

k. identifying in the $T_2$ distribution curve of the standardized sample the peak corresponding to the water protons of which the $T_2$ is averaged by exchange between the bulk water phase and the surface of the defibrillated primary cell wall material and identifying in the $T_2$ distribution curve of the matrix reference sample the peak corresponding to the bulk water phase;

l. calculating $T_2$ (sample), which is defined as the weighted average $T_2$ value for the identified peak in the $T_2$ distribution curve of the standardized sample and similarly calculating $T_2$ (matrix) which is defined as the weighted average $T_2$ value for the identified peak in the $T_2$ distribution curve of the matrix reference sample;

m. calculating the values of $R_2$(sample) and $R_2$(matrix), where:

$R_2$(sample)=1/$T_2$(sample), and $R_2$(matrix)=1/$T_2$(matrix);

n. calculating the FAP of the fiber mass as

FAP=$R_2$(sample)−$R_2$(matrix).

The CPMG T: relaxation pulse sequence is well-known in the field of NMR spectroscopy (See *Effects of diffusion on free precession in nuclear magnetic resonance experiments*, Carr, H. Y., Purcell, E. M., *Physical Review*, Volume 94, Issue 3, 1954, Pages 630-638/*Modified spin-echo method far measuring nuclear relaxation times*, Meiboom, S., Gill, D., *Review of Scientific Instruments*, Volume 29, Issue 8, 1958, Pages 688-691). Suitable time domain NMR spectrometers to perform this type of spectroscopy are well-known. Similarly, the usual measures to ensure the recording of reliable data are well-known in the field of time domain NMR spectroscopy. For example, the electromagnetic field should be sufficiently homogeneous at the locus where the sample volumes are placed. The field homogeneity can for example be checked by verifying whether a reference sample of pure water, yields a $T_2^*$ (T-two-star) for water protons of more than 2 milliseconds. The inverse Laplace transformation of step j may suitably be carried out using a non-negative least square constraints algorithm lsqnonneg (Lawson, C. L. and R. J. Hanson, *Solving Least Squares Problems*. Prentice-Hall, 1974. Chapter 23, p. 161), with the regularization parameter lambda set to 0.2. Software packages suitable for implementing the algorithm and carrying out the transform are well-known, Matlab being an example of such software.

In step k the peak that is selected in the $T_2$ distribution curve of the standardized sample, typically is the dominant peak, if the system is sufficiently homogeneous. In general, the peak that should be selected in the $T_2$ distribution curve is that corresponding to water protons of which the $T_2$ is averaged by diffusion and chemical exchange between bulk and surface sites of the dispersed citrus fiber material. This peak is particularly well-defined if the citrus fibre material is evenly distributed over the standardized sample. In most typical cases, there will be only one such peak, as can be seen in the examples in the Examples section below.

The weighted average $T_2$ in step l is for example suitably calculated by the summation $$\frac{\sum I(T_2) \cdot T_2}{\sum I(T_2)}$$

Here, $I(T_2)$ is the intensity at value $T_2$ and both summations are over the width of the peak.

A preferred way of establishing the FAP for the citrus fiber material is by following the protocol in the way described in the Examples section below. The above protocol and the Examples provide methods of measuring the FAP. However, the FAP may also be determined by a different protocol, as long as that protocol would lead to the same physical result, i.e. it would yield the same FAP for a particular citrus fibre material as the above protocol.

In summary, the FAP that is determined as described here thus provides a measure for the degree to which the fibers in the citrus fiber material are available for redispersion.

The citrus fibres in dry form according to the sixth aspect of the invention preferably have a FAP of at least 0.35 Hz and more preferably of at least 0.37 Hz. The citrus fibers preferably have a FAP of at most 5.0 Hz, more preferably at most 3.0 Hz and even more preferably at most 2.0 Hz.

The composition of matter in dry form according to the seventh aspect of the present invention preferably has a FAP of at least 0.60 Hz, more preferably of at least 0.70 Hz and even more preferably at least 0.74 Hz. The composition of matter preferably has a FAP of at most 5.0 Hz, more preferably at most 3.0 Hz and even more preferably at most 2.0 Hz. The preferences and examples regarding the citrus fiber, the type and amount of additive in the composition of matter according to this aspect of the invention are as presented hereinabove for the composition of matter in dry form comprising citrus fibers and an additive distributed between said fibres according to the present invention. It is particularly preferred that the additive is sucrose and that the ratio A:F of additive to citrus fiber is 0.10 to 1.0 and 3.0 to 1.0 by weight.

In an eight aspect, the present invention provides cellulose fibers in dry form having a self-suspending capacity (SSC) of at least 5%. The preferred cellulose fibers are citrus fibers. To inventors' knowledge, no cellulose or citrus fibers produced hitherto had a SSC as high as the fibers of the invention. Preferably, the SSC of the dry cellulose fibers is at least 8%, more preferably at least 12%, even more preferably at least 15%, yet even more preferably at least 17%, and most preferably at least 19%. Preferably, the moisture content of the dry cellulose fibers is at most 20 wt % relative to the total mass of fibers, more preferably at most 12 wt %, even more preferably at most 10 wt %, most preferably at most 8 wt %. The SSC of fibers may give an indication on how stable may be a dispersion of said fibers in an aqueous media. A higher SSC of fibers may thus indicate that aqueous dispersions containing thereof have improved stabilities.

The "self-suspending capacity" of a citrus fibre material may be determined using the following protocol:
a. providing the citrus fibre material in a particulate form wherein the particles can pass a 500 tim sieve; by milling the citrus fibre material using a Waring 8010EG laboratory blender equipped with an SS110 Pulverizer Stainless Steel Container using its low speed setting (18000 rpm) for 4 plus or minus 1 seconds; sieving the milled material using an AS200 digital shaker from Retsch GmbH Germany with a sieve set of 10 mm, 500 μm, 250 μm and 50 μm sieves, whilst shaking for 1 minute at an amplitude setting of 60; remilling and resieving the particles larger than 500 μm until they passed the 500 μm sieve and combining the sieved fractions;
b. preparing a dispersion of the citrus fibre material, comprising the fibres contained in the citrus fibre material at a concentration of 0.1 wt-% by agitating the sample using a Silverson overhead mixer equipped with an Emulsor screen having round holes of 1 mm diameter at 3000 rpm for 120 seconds;
c. filling a 100 ml graded glass measuring cylinder with 100 ml of said dispersion;
d. closing the cylinder and gently turning it up and down for 10 times to ensure a proper wetting of the citrus fiber material
e. allowing the citrus fiber material to settle for 24 hours at room temperature
f. visually determining the volume occupied by the cell fiber material suspension
g. calculating the SSC by expressing the volume of step e. as a percentage of the total volume.

Step a. of the above protocol serves to facilitate efficient dispersion during step b. The citrus fibre material in dry form may come at a variety of particle sizes. Therefore, step a. includes milling of the citrus fibre material so as to obtain the fibres in the specified particulate form. Suitable milling is provided by dry milling using a laboratory-scale Waring blender. In step b., the Silverson overhead mixer preferably is an L4RT overhead mixer.

The volume occupied in step f. is suitably determined by optical inspection. In step g., if for example the volume occupied by the cell wall material suspension is 80 ml, this is expressed as a self-suspending capacity SSC of 80%.

In a ninth aspect, the present invention provides cellulose fibers in dry form having a yield stress (YS) of at least 2.0 Pa, said YS being measured on an aqueous medium containing an amount of 2 wt % citrus fibers dispersed therein under a low-shear stirring of less than 10000 rpm. YS is measured on an aqueous medium containing an amount of 2 wt % of citrus fibers, i.e. relative to the total weight of the aqueous medium. The preferred cellulose fibers are citrus fibers. In a preferred embodiment, the fibers are dispersed under a low shear stirring of at most 3000 rpm. In another preferred embodiment, the fibers are dispersed under a low shear stirring of between 7000 rpm and 10000 rpm, more preferably about 8000 rpm and the YS of the dry cellulose fibers is at least 3.0, more preferably at least 7.0, most preferably at least 10.0. Preferably, the moisture content of the dry cellulose fibers is at most 20 wt % relative to the total mass of fibers, more preferably at most 12 wt %, even more preferably at most 10 wt %, most preferably at most 8 wt %. The YS may give an indication of the fibers' capacity to influence the viscoelastic properties of a dispersion containing thereof. A higher YS may indicate that a lower amount of fibers may be needed to achieve certain viscoelastic properties. To inventors' knowledge, no cellulose or citrus fibers produced hitherto and processed into a dispersion under the conditions presented hereinabove (e.g. rpm, fiber concentration, etc.) had the ability to provide a dispersion containing thereof with YS values as high as those provided by the present invention.

In a tenth aspect, the present invention provides citrus fibers in dry form, having a standardized yield stress (YS*) of at least 2.0 Pa wherein YS* is measured by
 a. providing the fibers in a particulate form wherein the particles can pass a 500 μm sieve, by milling the citrus fiber material using a Waring 8010EG laboratory blender equipped with an SS110 Pulverizer Stainless Steel Container using its low speed setting (18000 rpm) for 4 plus or minus 1 seconds; sieving the milled material using an AS200 digital shaker from Retsch GmbH Germany with a sieve set of 10 mm, 500 μm, 250 μm and 50 μm sieves, whilst shaking for 1 minute at an amplitude setting of 60; remilling and resieving the particles larger than 500 μm until they passed the 500 μm sieve and combining the sieved fractions;
 b. dispersing an amount of the fibers in particulate form so as to obtain 300 grams of an aqueous dispersion comprising 2 wt % of dry citrus fiber by weight of the dispersion, wherein the dispersion is buffered at pH 7.0, and whereby the fibers are dispersed using a Silverson overhead mixer equipped with an Emulsor screen having round holes of 1 mm diameter at 3000 rpm for 120 seconds; and
 c. using a parallel plate rheometer determining the shear storage modulus G' of the resultant dispersion as a function of the strain percentage and establishing the YS* from the maximum of the shear storage modulus G' versus the strain percentages.

Step a. of the above protocol for the determination of the YS* serves to facilitate efficient dispersion during step b. The citrus fiber in dry form may come at a variety of particle sizes. Therefore, step a. includes milling of the citrus fiber so as to obtain the fibers in the specified particulate form. Suitable milling is provided by dry milling using a laboratory-scale Waring blender. The buffered dispersion of step b. may be prepared using any suitable buffer system. Preferably, a phosphate-based buffer is used. In step c. the Silverson overhead mixer preferably is an L4RT overhead mixer. G' is measured using any suitable parallel plate rheometer, for example an ARG2 rheometer of TA Instruments. G' is measured at various strain levels as will be understood by the skilled person. A preferred way of establishing the YS* is by following the protocol in the way described below. The above protocol and the Examples provide methods of measuring the YS*. However, the YS* may also be determined by a different protocol, as long as that protocol would lead to the same physical result, i.e. it would yield the same YS* for a particular dry citrus fiber preparation as the above protocol.

The citrus fibres according to the tenth aspect of the invention preferably have a YS* of at least 2 Pa, more preferably at least 3 Pa, even more preferably at least 4 Pa and still more preferably at least 4.5 Pa. The citrus fibers preferably have a standardized yield stress of up to 50 Pa, and more preferably of up to 20 Pa. Thus it is particularly preferred that the citrus fibers in dry form have a standardized yield stress of between 2 Pa and 50 Pa, more preferably between 4 Pa and 20 Pa.

In an eleventh aspect, the present invention provides a composition of matter in dry form comprising citrus fibers and an additive distributed between said fibers, said composition having a transverse relaxation factor ("$R_2$") as measured by nuclear magnetic resonance ("NMR") of at least 0.70. Preferably, the $R_2$* value of said composition is at least 0.75, more preferably at least 0.80, even more preferably at least 0.85, most preferably at least 0.90. Preferably, the moisture content of said composition is at most 20 wt % relative to the total mass of fibers, more preferably at most 12 wt %, even more preferably at most 10 wt %, most preferably at most 8 wt %. Preferred examples and preferred amounts of the additive as well as suitable A:F ratios are presented above and will not be repeated herein.

In a twelfth aspect, the present invention provides a composition of matter in dry form comprising citrus fibers and an additive distributed between said fibers, said composition having a self-suspending capacity (SSC) of at least 9%. Preferably, the SSC of the composition is at least 13%, more preferably at least 15%, even more preferably at least 17%, yet even more preferably at least 19%, and most preferably at least 21%. Preferably, the moisture content of said composition is at most 20 wt % relative to the total mass of fibers, more preferably at most 12 wt %, even more preferably at most 10 wt %, most preferably at most 8 wt %. Preferred examples and preferred amounts of the additive as well as suitable A:F ratios are presented above and will not be repeated herein.

In an thirteenth aspect, the present invention provides a composition of matter in dry form comprising citrus fibers and an additive distributed between said fibers, said composition having a yield stress (YS) of at least 2.0 Pa, said YS being measured on an aqueous medium obtained by dispersing an amount of said composition therein under a low shear stirring of less than 10000 rpm to obtain a citrus fibers' concentration of 2 wt %. YS is measured on an aqueous medium containing an amount of 2 wt % of citrus fibers, i.e. relative to the total weight of the aqueous medium. Preferably, the YS is at least 3.0 Pa, more preferably at least 5.0 Pa, even more preferably at least 8.0 Pa, yet even more preferably at least 10.0 Pa, yet even more preferably at least 12.0 Pa, most preferably at least 14.0 Pa. Preferably, the moisture content of said composition is at most 20 wt % relative to the total mass of fibers, more preferably at most 12 wt %, even more preferably at most 10 wt %, most preferably at most 8 wt %. Preferred examples and preferred amounts of the additive as well as suitable A:F ratios are presented above and will not be repeated herein.

In a fourteenth aspect, the present invention provides a composition of matter in dry form comprising citrus fibers and an additive distributed between said fibers, said composition having, having a standardized yield stress (YS*) of at least 2.0 Pa wherein the YS* is measured by
 a. providing the composition in a particulate form wherein the particles can pass a 500 μm sieve, by milling the citrus fiber material using a Waring 8010EG laboratory blender equipped with an SS110 Pulverizer Stainless Steel Container using its low speed setting (18000 rpm) for 4 plus or minus 1 seconds; sieving the milled material using an AS200 digital shaker from Retsch GmbH Germany with a sieve set of 10 mm, 500 µm, 250 µm and 50 µm sieves, whilst shaking for 1 minute at an amplitude setting of 60; remilling and resieving the particles larger than 500 µm until they passed the 500 µm sieve and combining the sieved fractions;

b. dispersing an amount of the composition in particulate form so as to obtain 300 grams of an aqueous dispersion comprising 2 wt % of dry citrus fiber by weight of the dispersion, wherein the dispersion is buffered at pH 7.0, and whereby the fibers are dispersed using a Silverson overhead mixer equipped with an Emulsor screen having round holes of 1 mm diameter at 3000 rpm for 120 seconds; and c. using a parallel plate rheometer determining the shear storage modulus G' of the resultant dispersion as a function of the strain percentage and establishing the yield stress from the maximum of the shear storage modulus G' versus the strain percentages.

Step a. of the above protocol for the determination of the YS* serves to facilitate efficient dispersion during step b. The composition of matter in dry form may come at a variety of particle sizes. Therefore, step a. includes milling of the composition so as to obtain the composition in the specified particulate form. Suitable milling is provided by dry milling using a laboratory-scale Waring blender. The buffered dispersion of step b. may be prepared using any suitable buffer system. Preferably, a phosphate-based buffer is used. In step c. the Silverson overhead mixer preferably is an L4RT overhead mixer. G' is measured using any suitable parallel plate rheometer, for example an ARG2 rheometer of TA Instruments. G' is measured at various strain levels as will be understood by the skilled person. A preferred way of establishing the YS* is by following the protocol in the way described below. The above protocol and the Examples provide methods of measuring the YS*. However, the YS* may also be determined by a different protocol, as long as that protocol would lead to the same physical result, i.e. it would yield the same YS* for a particular dry citrus fiber preparation as the above protocol.

The composition of matter in dry form according to the fourteenth aspect of the invention preferably has a YS* of at least 2 Pa, more preferably at least 3 Pa, even more preferably at least 4 Pa and still more preferably at least 4.5 Pa. The composition of matter in dry form preferably has a standardized yield stress YS* of up to 50 Pa, and more preferably of up to 20 Pa. Thus it is particularly preferred that the composition of matter in dry form has a standardized yield stress YS* of between 2 Pa and 50 Pa, more preferably between 4 Pa and 20 Pa. The preferences and examples regarding the citrus fiber, the type and amount of additive in the composition of matter according to this aspect of the invention are as presented hereinabove for the composition of matter in dry form comprising citrus fibers and an additive distributed between said fibers according to the present invention.

In a fifteenth aspect, the present invention provides a dispersion comprising citrus fibers dispersed in an aqueous medium, said dispersion having a G' value of at least 50 Pa when measured at a fiber concentration of 2 wt % relative to the total mass of the dispersion. Preferably, said G' is at least 100 Pa, more preferably at least 150 Pa, even more preferably at least 200 Pa, yet even more preferably at least 250 Pa, most preferably at least 350 Pa. Preferably, said dispersion has a yield stress (YS) of at least 2.0 Pa, more preferably at least 3.0 Pa, even more preferably at least 5.0 Pa, yet even more preferably at least 8.0 Pa, yet even more preferably at least 10.0 Pa, yet even more preferably at least 12.0 Pa, most preferably at least 14.0 Pa. Examples of dispersions include without limitation suspensions, emulsions, foams and the like. The citrus fibers in the dispersion may have a Brownian motion or they may be fixed at an interface present in the aqueous medium.

In a sixteenth aspect, the present invention provides a method for manufacturing the inventive fibers and/or compositions comprising the steps of:

a. Homogenizing an aqueous slurry of a source of citrus fibers to obtain an aqueous slurry of citrus fibers;

b. Contacting the aqueous slurry of citrus fibers with an organic solvent to obtain a precipitate phase and a liquid phase; wherein the precipitate is in the form of granules;

c. Separating said precipitate phase from the liquid phase to obtain a semi-dry citrus fiber cake having a dry substance-content of at least 10 wt % relative to the mass of said cake;

d. Comminuting said cake to obtain grains containing citrus fibers; and mixing said grains with an additive to obtain a semi-dry composition comprising citrus fibers and an additive; and e. Desolventizing and/or dehydrating said semi-dry composition to obtain a dry composition containing citrus fibers and an additive and having a moisture content of preferably below 20 wt % relative to the total weight of the fibers.

It is difficult to prepare a dry composition containing citrus fibers without affecting the composition's dispersibility in an aqueous media. This difficulty is attributed to many factors (collectively referred to in literature as "hornification") such as the formation of hydrogen bonds and/or lactone bridges between the fibers. Hornification typically reduces the available free-surface area of the fibers and/or strengthens the linkage between the fibers, which in turn may reduce the capacity of the fibers to absorb liquid and thus to disperse. Compositions containing hornified dry citrus fibers either cannot be dispersed into an aqueous medium, e.g. water, a water solution or a water suspension, or they can be dispersed only by using high or ultra-high shear mixing.

The method of the invention succeeded however in producing dry compositions wherein the hornification of the citrus fibers was largely prevented. Without being bound to any theory the inventors believe that any of the G', $R_2$*, SSC and YS as well as the reduced deviations of STDEV from MAX characteristic to the inventive fibers and inventive compositions may indicate a reduced hornification of said fibers.

The method of the invention (the inventive method), contains a step of homogenizing an aqueous slurry of a source of citrus fibers ("source slurry"). The source of citrus fibers may be citrus peel, citrus pulp, citrus rag or combinations thereof. The source of citrus fibers may be a by-product obtained during the pectin extraction process. Preferably, the source of the citrus fibers is citrus peel; more preferably is de-pectinized citrus peel. Said source slurry preferably comprises a dry substance content of at least 2 wt %, more preferably at least 3 wt %, more preferably at least 4 wt %. Preferably said dry substance content of said source slurry is at most 10 wt %, more preferably at most 8 wt %, most preferably at most 6 wt %.

The homogenization of the source slurry may be carried out with a number of possible methods including, but not limited to, high shear treatment, pressure homogenization, cavitation, explosion, pressure increase and pressure drop treatments, colloidal milling, intensive blending, extrusion, ultrasonic treatment, and combinations thereof.

In a preferred embodiment, the homogenization of the source slurry is a pressure homogenization treatment which may be carried out with a pressure homogenizer. Pressure homogenizers typically comprise a reciprocating plunger or piston-type pump together with a homogenizing valve assembly affixed to the discharge end of the homogenizer. Suitable pressure homogenizers include high pressure homogenizers manufactured by GEA Niro Soavi of Parma (Italy), such as the NS Series, or the homogenizers of the Gaulin and Rannie series manufactured by APV Corporation of Everett, Mass. (US). During the pressure homogenization, the source slurry is subjected to high shear rates as the result of cavitation and turbulence effects. These effects are created by the source slurry entering a homogenizing valve assembly which is part of a pump section of the homogenizer at a high pressure (and low velocity). Suitable pressures for the inventive method are from 50 bar to 2000 bar, more preferably between 100 bar and 1000 bar. While not being bound to any theory, it is believed that the homogenization causes disruptions of the source of citrus fibers and its disintegration into the fibrous component.

Depending on the particular pressure selected for the pressure homogenization, and the flow rate of the source slurry through the homogenizer, the source slurry may be homogenized by one pass through the homogenizer or by multiple passes. In one embodiment, the source slurry is homogenized by a single pass through the homogenizer. In a single pass homogenization, the pressure used is preferably from 300 bars to 1000 bars, more preferably from 400 bars to 900 bars, even more preferably from 500 bars to 800 bars. In another preferred embodiment, the source slurry is homogenized by multiple passes through the homogenizer, preferably at least 2 passes, more preferably at least 3 passes through the homogenizer. In a multi-pass homogenization, the pressure used is typically lower compared to a single-pass homogenization and preferably from 100 bars to 600 bars, more preferably from 200 bars to 500 bars, even more preferably from 300 bars to 400 bars.

The result of the homogenization step is an aqueous slurry of citrus fibers ("fiber slurry") comprising a dry substance content of fibers in essentially the same amount as the source slurry. Said fiber slurry is then contacted with an organic solvent. Said organic solvent should preferably be polar and water-miscible to better facilitate water removal. Examples of suitable organic solvents which are polar and water-miscible include, without limitation, alcohols such as methanol, ethanol, propanol, isopropanol and butanol. Ethanol and isopropanol are preferred organic solvents; isopropanol is the most preferred organic solvent for use in the inventive method. The organic solvent can be used in its 100% pure form or may be a mixture of organic solvents. The organic solvent can also be used as a mixture of the organic solvent and water, hereinafter referred to as an aqueous solvent solution. The concentration of organic solvent in said aqueous solvent solution is preferably from about 60 wt % to about 100 wt % relative to the total weight of said solution, more preferably between 70 wt % and 95 wt %, most preferably between 80 wt % and 90 wt %. In general, lower concentrations of the organic solvent are suitable to remove water and water-soluble components whereas increasing the concentration of said organic solvent also helps in removing oil and oil-soluble components if desired. In one embodiment, an organic solvent mixture containing a non-polar organic (NPO) co-solvent and the organic solvent or the aqueous solvent solution is used in the inventive method. The utilization of the organic solvent mixture may improve for example the recovery of oil-soluble components in the citrus pulp. Examples of suitable NPO co-solvents include, without limitation, ethyl acetate, methyl ethyl ketone, acetone, hexane, methyl isobutyl ketone and toluene. The NPO co-solvents are preferably added in amounts of up to 20% relative to the total amount of organic solvent mixture.

The fiber slurry is contacted with the organic solvent preferably in a ratio slurry:solvent of at most 1:8, more preferably at most 1:6, or most preferably at most 1:4. Preferably said ratio is at least 1:0.5, more preferably at least 1:1, most preferably at least 1:2. Preferably, said fiber slurry is contacted with the organic solvent for at least 10 minutes, more preferably for at least 20 minutes, most preferably for at least 30 minutes. Preferably, said slurry is contacted with the organic solvent for at most several hours, more preferably for at most 2 hours, most preferably for at most 1 hour.

According to the invention, said fiber slurry is contacted with said organic solvent to obtain a precipitate phase and a liquid phase. The inventors observed that during contacting the organic solvent with the fibers slurry, the fiber slurry releases at least part of its water content into the organic solvent which in turn causes the citrus fibers to precipitate. By "precipitate phase" is herein understood a phase containing the majority of the citrus fibers, e.g. more than 80% of the total amount of fibers, preferably more than 90%, most preferably more than 98% and also containing organic solvent and water. The precipitate phase usually settles due to gravity forces. The precipitate phase typically has a solid- or a gel-like appearance, i.e. it essentially maintains its shape when placed on a supporting surface. By "liquid phase" is herein understood a phase containing organic solvent and water. The liquid phase may also contain some citrus fibers which did not precipitate. According to the invention, the precipitate phase is in the form of granules, preferably, millimeter-size granules. Preferred granule sizes are between 1 mm and 100 mm, more preferably between 5 mm and 50 mm. By "the size of a granule" is herein understood the biggest dimension of said granule. The formation of the precipitate phase into granules may be achieved for example by bringing the fiber slurry under agitation into a container containing the organic solvent or by pouring said slurry in the organic solvent. The amount of agitation typically dictates the size of the formed granules. It was observed that by forming granules, the subsequent water removal from said granules is facilitated. Without being bound to any theory, it is believed that the formation of granules also aids in preserving and/or increasing the free surface area of the citrus fibers available for water binding and may also avoid a collapse of the fibers.

The precipitate phase is subsequently separated from the liquid phase to obtain a semi-dry citrus fibers cake ("fiber cake"). Said separation can be achieved using known methods such as centrifugation, filtration, evaporation and combinations thereof.

To increase the dry substance content, steps b) and c) of the inventive method can be repeated at least one time, preferably before carrying out step d). The fiber cake can also be subjected to an extraction step. A preferred extraction method is pressing, e.g. with a normal press, a screw press or an extruder. A more preferred extraction method is pressure filtration using a volume chamber filter press or a membrane filter press; pressure filters being sold for example by BHS Sonthofen, DE. Two-sided liquid removal is recommended for the pressure filtration since more filtering area is available per volume of the fiber cake.

The fiber cake is semi-dry, i.e. it has a dry substance content of preferably at least 10 wt %, more preferably of at least 15 wt %, or most preferably of at least 20 wt % relative to the mass of said cake. Preferably, said cake has a liquid-content of at most 50 wt %, more preferably at most 40 wt %, most preferably at most 30 wt % relative to the total mass of said cake. The liquid typically contains organic solvent and water.

In accordance with the invention, the fiber cake is comminuted to obtain grains containing citrus fibers ("fiber grains"), said grains preferably having a diameter of at most 100 mm, more preferably at most 50 mm, even more preferably at most 30 mm, yet even more preferably at most 10 mm, yet even more preferably at most 5 mm, most preferably at most 3 mm. With "grain diameter" is herein understood the largest dimension of the grain. The diameter may be determined using a microscope equipped with graticule. Cutters may be used to cut the fiber cake into grains. Alternatively, the fiber cake can subjected to milling and/or grinding in order to form it into grains. Examples of suitable means to comminute the fiber cake include without limitation a cutter mill, a hammer mill, a pin mill, a jet mill and the like.

The fiber grains are mixed with an additive to obtain a semi-dry composition comprising citrus fibers and the additive. Examples of suitable additives as well as preferred choices are given above and will not be repeated herein. Mixing the fiber grains with the additive can be effected with known means in the art, examples thereof including without limitation a malaxer, a transport screw, an air-stream agitation mixer, a paddle mixer, a Z-mixer, a tumble mixer, a high speed paddle mixer, a power blender and the like. The additive may be provided in a solid form or in solution. Preferably, the additive is provided in a solid form, more preferably as a powder, even more preferably as a powder having an average particle size ("APS") of between 100 and 500 μm, more preferably between 150 and 300 μm; the APS can be determined by ASTM C136-06.

The semi-dry composition is subjected to a desolventizing and/or dehydrating step wherein the organic solvent and/or the water are extracted from said composition. Preferably, the inventive method contains both steps of desolventizing and dehydration. It was surprisingly observed that during the organic solvent and/or water extraction, the hornification of citrus fibers was largely prevented. Without being bound to any theory, the inventors attributed the reduced hornification to the careful pre-processing of the composition prior to said extraction as detailed in steps a) to d) of the inventive method.

Desolventisation and dehydration of said composition can be carried out with a desolventizer which removes organic solvent and/or water from the composition and may also enable the organic solvent to be reclaimed for future use. Desolventizing also ensures that the obtained dry composition is safe for milling and commercial use. The desolventizer can employ indirect heat to remove the organic solvent from the composition; the advantage of using said indirect heat is that significant amounts of organic solvents can be extracted. Also, direct heat can be provided for drying, e.g. by providing hot air from flash dryers or fluidized bed dryers. Direct steam may be employed, if desired, to remove any trace amounts of organic solvent remaining in the composition. Vapors from the desolventizer preferably are recovered and fed to a still to reclaim at least a portion of the organic solvent.

Retention times for the desolventizing and/or dehydrating step may vary over a wide range but can be about 5 minutes or less. Suitable temperatures at which said desolventizing and dehydrating step is carried out depend on such factors as the type of organic solvent and most often ranges from about 4° C. to about 85° C. at atmospheric pressure. Temperatures can be appropriately increased or decreased for operation under supra- or sub-atmospheric pressures. Optionally, techniques such as ultrasound are used for enhancing efficiency of the desolventizing and dehydrating. By maintaining a closed system, solvent losses can be minimized. Preferably, at least about 70 wt % of the organic solvent is recovered and reused.

Dehydration can be effected with known means in the art, examples thereof including without limitation paddle driers, fluidized bed driers, stirred vacuum driers, drum driers, plate driers, belt driers, microwave driers and the like. Preferably, the dehydration temperature is at most 100° C., more preferably at most 80° C. most preferably at most 60° C. Preferably, the dehydration temperature is at least 30° C., more preferably at least 40° C., most preferably at least 50° C.

The desolventizing and/or dehydrating step are carried out to obtain a dry composition comprising citrus fibers and an additive, said dry composition having a moisture content of at most 20 wt % relative to the total weight of the fibers, preferably at most 15 wt %, more preferably at most 12 wt %, even more preferably at most 10 wt %, most preferably at most 8 wt %.

Optionally, the method of the invention further comprises a step of removing said additive and/or classifying the dry composition to obtain the desired particle size and/or packing the dry composition.

In a preferred embodiment, the inventive method comprises a classification step of the dry composition which may improve the homogeneity of the powder, narrow particle size distribution and improve degree of rehydration. Classification may be carried out using either a static or dynamic classifier. The inventive method may further comprise a packaging step of the dry composition.

In another preferred embodiment, the additive is extracted from the dried and/or classified composition as obtained at steps f) and/or g), respectively to obtain dry citrus fibers. To aid in the extraction of the additive, preferably, an additive is used that has a boiling point of less than the degradation temperature of the citrus fibers. The extraction may be performed by washing the additive with a suitable solvent other than water. The extraction is preferably performed by subjecting said composition to an extraction temperature between the boiling point of the additive and the degradation temperature of the citrus fibers and allowing the additive to evaporate; preferably the evaporation is carried out under vacuum. Preferably, said additive has a boiling point of at most 250° C., more preferably at most 200° C., most preferably at most 150° C. The boiling points of various materials are listed in the CRC Handbook of Chemistry and Physics or alternatively. ASTM D1120 may be used to determine said boiling point. Preferably the extraction temperature is between 100 and 300° C., more preferably between 100 and 250° C., most preferably between 100 and 200° C. Examples of additives having such reduced boiling points include low molecular weight polyols, e.g. polyether polyols, ethylene glycols, and the like. By low molecular weight is herein understood an M of between 50 and 500.

The use of such extractable additives enables the manufacturing of the inventive fibers. Alternatively, dry citrus fibers may be obtained with the inventive method by skipping in step d) the addition of the additive by mixing. Dry cellulose fibers may also be obtained with the method of the invention by choosing an appropriate source of cellulose fibers to be processed.

The dry composition comprising the citrus fibers and the additive is preferably milled and/or classified to obtain a powder having an average particle size of preferably at least 50 μm, more preferably at least 150 μm, most preferably at least 250 μm. Preferably said average particle size is at most 2000 μm, more preferably at most 1000 μm, most preferably at most 500 μm. Said average particle size may be determined by ASTM C136-06.

In a seventeenth aspect, the invention relates to a composition of matter in dry form obtainable by the method for manufacturing the composition according to the sixteenth aspect of the present invention.

The invention will be further detailed in the following exemplary embodiments, without being however limited thereto.

In a first embodiment, the inventive composition of matter in dry form comprises citrus fibers and an additive distributed between said fibers, wherein said composition has a transverse relaxation factor ($R_2^*$) of at least 0.70, more preferably of at least 0.75, more preferably of at least 0.85, most preferably of at least 0.90, wherein when dispersing said composition with a low shear stirring of less than 10000 rpm in an aqueous medium to yield a fiber concentration of 2 wt %, the obtained dispersion has a G' value of at least 50 Pa. Preferably, the dispersion is carried out with a low shear stirring of at most 8000 rpm, more preferably at most 5000 rpm, most preferably at most 3000 rpm. Preferably, the A:F ratio of the composition is between 0.01:1 and 10:1 by weight, more preferably between 0.1:1 and 9:1 by weight, most preferably between 0.4:1 and 8:1 by weight. Preferably, the citrus fibers did not undergo any substantial chemical modification. Preferably, the additive is chosen from the group consisting of fructose, mannose, galactose, glucose, talose, gulose, allose, altrose, idose, arabinose, xylose, lyxose, ribose, sucrose, maltose, lactose, glycerol, sorbitol, starch and combinations thereof.

In a second embodiment, the inventive composition of matter in dry form comprises citrus fibers and an additive distributed between said fibers, wherein said composition has a SSC of at least 9% and a transverse relaxation factor ($R_2^*$) of at least 0.70. Preferably, the SSC of the composition is at least 13%, more preferably at least 15%, even more preferably at least 17%, yet even more preferably at least 19%, and most preferably at least 21%. Preferably, the $R_2^*$ value of said composition is at least 0.75, more preferably at least 0.80, even more preferably at least 0.85, most preferably at least 0.90. Preferably, the A:F ratio of the composition is between 0.01:1 and 10:1 by weight, more preferably between 0.1:1 and 9:1 by weight, most preferably between 0.4:1 and 8:1 by weight. Preferably, the citrus fibers did not undergo any substantial chemical modification. Preferably, the additive is chosen from the group consisting of fructose, mannose, galactose, glucose, talose, gulose, allose, altrose, idose, arabinose, xylose, lyxose, ribose, sucrose, maltose, lactose, glycerol, sorbitol, starch and combinations thereof.

In a third embodiment, the citrus fibers of the invention have a transverse relaxation factor ("$R_2^*$") as measured by nuclear magnetic resonance ("NMR") of at least 0.7 and a self-suspending capacity (SSC) of at least 9%. Preferably, the $R_2^*$ value of said dry cellulose fibers is at least 0.9, even more preferably at least 1.1, and most preferably at least 1.2. Preferably, the SSC of the dry cellulose fibers is at least 12, even more preferably at least 15, yet even more preferably at least 17 and most preferably at least 19. Preferably, the moisture content of the dry citrus fibers is at most 20 wt % relative to the total mass of fibers, more preferably at most 12 wt %, even more preferably at most 10 wt %, most preferably at most 8 wt %.

In a fourth embodiment, the invention relates to citrus fibers in dry form having a storage modulus (G') of at least 50 Pa, said G' being measured on an aqueous medium containing an amount of 2 wt % citrus fibers dispersed therein under a low-shear stirring of less than 10000 rpm, said fibers preferably having a transverse relaxation factor ("$R_2^*$") as measured by nuclear magnetic resonance ("NMR") of at least 0.35, said fibers preferably having a self-suspending capacity (SSC) of at least 5%, said fibers preferably having a yield stress (YS) of at least 2.0 Pa, said YS being measured on an aqueous medium containing an amount of 2 wt %° citrus fibers dispersed therein under a low-shear stirring of less than 10000 rpm. Preferably, said G' is at least 75 Pa, more preferably at least 100 Pa, even more preferably at least 125 Pa, yet even more preferably at least 150 Pa, most preferably at least 170 Pa. Preferably, the stirring used to achieve the dispersion of said citrus fibers in the aqueous medium is at most 8000 rpm, more preferably at most 5000 rpm, most preferably at most 3000 rpm. Preferably, said citrus fibers contain an amount of water of at most 12 wt %, more preferably at most 10 wt %, or most preferably at most 8 wt %. Preferred ranges for $R_2^*$, SSC and YS are presented herein above where the third, fourth and fifth aspects of the invention, respectively, are detailed and will not be further repeated herein.

In a fifth embodiment, the invention relates to a composition of matter in dry form comprising citrus fibers and an additive distributed between said fibers, said composition having a storage modulus (G') of at least 50 Pa, said G' being measured on an aqueous medium obtained by dispersing an amount of said composition therein under a low shear stirring of less than 10000 rpm to obtain a citrus fibers' concentration of 2 wt % relative to the total amount of the aqueous medium, said composition preferably having a transverse relaxation factor ("$R_2^*$") as measured by nuclear magnetic resonance ("NMR") of at least 0.70, said composition preferably having a self-suspending capacity (SSC) of at least 9%, said composition preferably having a yield stress (YS) of at least 2.0 Pa, said YS being measured on an aqueous medium obtained by dispersing an amount of said composition therein under a low shear stirring of less than 10000 rpm to obtain a citrus fibers' concentration of 2 wt %. Preferably, the composition contains an amount of water of at most 12 wt %, more preferably at most 10 wt %, or most preferably at most 8 wt %. Preferably, the composition has an additive:fiber (A:F) ratio of between 0.01:1.0 and 10.0: 1.0 by weight, more preferably between 0.1:1.0 and 9.0:1.0 by weight, most preferably between 0.4:1.0 and 8.0:1.0 by weight. Preferably, the additive is chosen from the group consisting of glucose, sucrose, glycerol and sorbitol. Preferred ranges for G', $R_2^*$, SSC and YS are presented herein above where the second, sixth, seventh and eighth aspects of the invention, respectively, are detailed and will not be further repeated herein.

It was observed that the inventive compositions have an optimal viscoelastic stability, e.g. fewer fluctuations of compositions' viscoelastic behavior. The ability of the inventive compositions to smoothen out viscoelastic fluctuations may enable a more reliable processing thereof, which in turn may lead to optimal quality of various products containing said composition, e.g., food, feed, personal care and pharmaceutical products.

The inventive fibers and the inventive compositions are suitably used in the production of a large variety of food compositions. Examples of food compositions comprising thereof, to which the invention relates, include: luxury drinks, such as coffee, black tea, powdered green tea, cocoa, adzuki-bean soup, juice, soya-bean juice, etc.; milk component-containing drinks, such as raw milk, processed milk, lactic acid beverages, etc.: a variety of drinks including nutrition-enriched drinks, such as calcium-fortified drinks and the like and dietary fiber-containing drinks, etc.; dairy products, such as butter, cheese, yogurt, coffee whitener, whipping cream, custard cream, custard pudding, etc.; iced products such as ice cream, soft cream, lacto-ice, ice milk, sherbet, frozen yogurt, etc.; processed fat food products, such as mayonnaise, margarine, spread, shortening, etc.; soups; stews; seasonings such as sauce, TARE, (seasoning sauce), dressings, etc.; a variety of paste condiments represented by kneaded mustard; a variety of fillings typified by jam and flour paste; a variety or gel or paste-like food products including red bean-jam, jelly, and foods for swallowing impaired people; food products containing cereals as the main component, such as bread, noodles, pasta, pizza pie, corn flake, etc.; Japanese, US and European cakes, such as candy, cookie, biscuit, hot cake, chocolate, rice cake, etc.; kneaded marine products represented by a boiled fish cake, a fish cake, etc.; live-stock products represented by ham, sausage, hamburger steak, etc.; daily dishes such as cream croquette, paste for Chinese foods, gratin, dumpling, etc.; foods of delicate flavor, such as salted fish guts, a vegetable pickled in sake lee, etc.; liquid diets such as tube feeding liquid food, etc.; supplements; and pet foods. These food products are all encompassed within the present invention, regardless of any difference in their forms and processing operation at the time of preparation, as seen in retort foods, frozen foods, microwave foods, etc.

The invention also provides a food composition in dry form, comprising the citrus fibre according to the invention and/or the composition of matter in dry form according to the invention. Such a food composition in dry form preferably comprises a composition of matter in dry form, wherein said composition of matter comprises citrus fibres and an additive distributed between said fibres. It is particularly preferred that the additive is sucrose and that the ratio A:F of additive to citrus fibre is 0.10 to 1.0 and 3.0 to 1.0 by weight.

It was surprisingly found that the citrus fibres in dry form of the present invention and the composition in dry form comprising citrus fibres and an additive of the present invention can be readily dispersed in an aqueous medium. Therefore, these fibres and compositions can advantageously be used in the manufacture of compositions comprising dispersed citrus fibres. Traditionally, exploitation of the properties of citrus fibres to prepare a composition with excellent rheological properties requires the use of equipment that can impart high to very high shear during the manufacture of the composition. Such equipment is usually costly, and in operation uses a relatively large amount of energy. Moreover, such high shear levels may be detrimental to the properties of other constituents of such a composition. In particular if the product is a food product, for instance, high shear treatment may adversely affect the taste, flavour and/or other organoleptic properties provided by other ingredients. Using the citrus fibres or composition in dry form comprising citrus fibres of the present invention allows the manufacture of intermediate or end products with dispersed citrus fibres whilst requiring a lower amount of shear energy to obtain the same or even better benefits of dispersed citrus fibres in the manufactured product. Thus, the citrus fibres and composition of matter in dry form of the present invention provide increased flexibility and efficiency in such product manufacture.

Consequently, the present invention in an eighteenth aspect provides a method for preparing a composition comprising an aqueous phase wherein the aqueous phase comprises dispersed citrus fibres, wherein the method comprises the step of dispersing a source of citrus fibres in an aqueous medium thereby to form at least part of said first aqueous phase; and wherein the source of citrus fibres is citrus fibres in dry form according to the present invention or the composition in dry form comprising citrus fibres and an additive distributed between said fibres according to the present invention. The aqueous phase may be prepared with a variety of rheological properties, and may for instance be selected to have any consistency between highly fluid (water thin) to a highly viscous, or spoonable, or gelled consistency. The level of citrus fibre in the aqueous phase may suitably be adjusted to the rheological requirements for the particular product. Typically, the aqueous phase may comprise between 0.01 and 10 wt-% of dispersed citrus fibres with respect to the weight of the aqueous phase, and preferably comprises between 0.05 and 5 wt-%, even more preferably between 0.1 and 3 wt-% of dispersed citrus fibres. The source of citrus fibres that is used in the present method preferably is a composition of matter in dry form comprising citrus fibre and an additive distributed between said citrus fibres. It is particularly preferred that the additive is sucrose and that the ratio A:F of additive to citrus fibre is 0.10 to 1.0 and 3.0 to 1.0 by weight. It is likewise preferred that the composition of citrus fibre used as the source of citrus fibre has a Fibre Availability Parameter of at least 0.70 Hz, more preferably 0.8 Hz and even more preferably at least 0.9 Hz.

The present method is particularly useful in the preparation emulsified products. Therefore, the method preferably is a method for preparing a composition in the form of an oil-in-water emulsion. The oil-in-water emulsion is preferably an edible emulsion. The edible oil-in-water emulsion preferably comprises from 5 to 50 wt-% of oil. The oil typically is an edible oil. As understood by the skilled person such edible oils typically comprise triglycerides, usually mixtures of such triglycerides. Typical examples of edible oils include vegetable oils including palm oil, rapeseed oil, linseed oil, sunflower oil and oils of animal origin.

The present method is also useful to prepare emulsions in the form of a dressing or a similar condiment, because it is suitable to provide rheological properties that are generally considered desirable for dressings. Since such dressings are typically acidic in nature, the present method is preferably for preparing a composition in the form of an oil-in-water emulsion wherein the composition in the form of an oil-in-water-emulsion comprises from 15 to 50 wt-% of oil and from 0.1 to 10 wt-% of acid. It is particularly preferred that the composition in the form of an oil-in-water emulsion is a mayonnaise.

The present method is also useful in the preparation of emulsified products which comprise proteins. Thus, the method is preferably a method for preparing a composition in the form of an oil-in-water emulsion, wherein the composition in the form of an oil-in-water emulsion comprises protein, wherein the amount of protein is preferably from 0.1 to 10 wt %, more preferably from 0.2 to 7 wt % and even more preferably from 0.25 to 4 wt % by weight of the composition. The protein may advantageously include milk protein, which is a desirable component in many food compositions. Thus, the protein preferably comprises at least 50 wt % milk protein, more preferably at least 70 wt %, even more preferably at least 90 wt % and still more preferably consists essentially of milk protein. The suitability of the present method to impart desirable characteristics deriving from citrus fibres to an aqueous medium, in the presence of both emulsified oil and milk protein, make the method suitable for the preparation of ready-to-drink milk teas. Hence, the present method preferably is a method for the preparing a composition in the form of an oil-in-water emulsion, wherein the composition in the form of an oil-in-water emulsion is a ready-to-drink tea-based beverage. The term "ready-to-drink tea beverage" refers to a packaged tea-based beverage, i.e. a substantially aqueous drinkable composition suitable for human consumption. Preferably the beverage comprises at least 85% water by weight of the beverage, more preferably at least 90%, Ready-to-drink (RTD) milk tea beverages usually contain milk solids like for example milk protein and milk fat that give the beverages certain organoleptic properties like for example a 'creamy mouthfeel'. Such an RTD milk tea beverage preferably comprises at least 0.01 wt %° tea solids on total weight of the beverage. More preferably the beverage comprises from 0.04 to 3 wt % tea solids, even more preferably from 0.06 to 2%, still more preferably from 0.08 to 1 wt % and still even more preferably from 0.1 to 0.5 wt %. The tea solids may be black tea solids, green tea solids or a combination thereof. The term "tea solids" refers to dry material extractable from the leaves and/or stem of the plant *Camellia sinensis*, including for example the varieties *Camellia sinensis* var. *sinensis* and/or *Camellia sinesis* var. *assamica*. Examples of tea solids include polyphenols, caffeine and amino acids. Preferably, the tea solids are selected from black tea, green tea and combinations thereof and more preferably the tea solids are black tea solids. In case the method is a method for the preparation of a RTD milk tea beverage, the source of citrus fibres that is used preferably is a composition of matter in dry form comprising citrus fibre and an additive distributed between said citrus fibres. It is particularly preferred that the additive is sucrose and that the ratio A:F of additive to citrus fibre is 0.10 to 1.0 and 3.0 to 1.0 by weight. It is likewise preferred that the composition of citrus fibre used as the source of citrus fibre has a Fibre Availability Parameter of at least 0.70 Hz, more preferably 0.8 Hz and even more preferably at least 0.9 Hz.

The present method is also useful for preparing edible compositions comprising an aqueous phase, which optionally comprise an oil-based constituent, but which do not require the presence of the oil-based constituent. Thus, the present method for preparing a composition wherein the composition comprises at least a first aqueous phase comprising dispersed citrus fibres preferably is a method for preparing a food composition comprising a flavour base and from 0 wt-% to 5 wt-% of oil, more preferably from 0 wt-% to 2 wt-%, even more preferably from 0 wt-% to 1 wt-% and even more preferably from 0 wt-% to 0.5 wt-% of oil with respect to the weight of the composition. Herein, "flavour base" means the base of the food composition that is responsible for the identification of the product. The flavour base preferably is a fruit- or vegetable-based product, or a mixture thereof. The present method is especially useful for imparting desirable rheological characteristics to tomato-based products. Therefore, more preferably the flavour base is a tomato paste, a tomato puree, a tomato juice, a tomato concentrate or a combination thereof, and even more preferably it is a tomato paste. Thus, present method for preparing a composition comprising an aqueous phase, preferably is a method for the preparation of a composition wherein the composition is a tomato sauce or a tomato ketchup.

The present method for preparing a composition, wherein the composition comprises an aqueous phase comprising dispersed citrus fibres is not limited to the preparation of edible or food compositions. The properties of the citrus fibres in dry form and the composition of matter in dry form of the present invention make the present method particularly suitable to impart desired rheological properties onto compositions comprising a surfactant system. Thus, the present invention also provides a method for preparing a composition comprising a surfactant system, wherein the composition comprises at least a first aqueous phase comprising dispersed citrus fibres, wherein the method comprises the step of dispersing a source of citrus fibres in an aqueous medium thereby to form at least part of said first aqueous phase; and wherein the source of citrus fibres is citrus fibres in dry form according to the present invention or the composition of matter in dry form comprising citrus fibres and an additive distributed between said fibres according to the present invention. Preferably, the source of citrus fibres is a composition of matter in dry from comprising citrus fibres and an additive distributed between said fibres. It is particularly preferred that the additive is sucrose and that the ratio A:F of additive to citrus fibre is 0.10 to 1.0 and 3.0 to 1.0 by weight. It is likewise preferred that the composition of citrus fibre used as the source of citrus fibre has a Fibre Availability Parameter of at least 0.70 Hz, more preferably 0.8 Hz and even more preferably at least 0.9 Hz.

The composition comprising a surfactant system preferably comprises the surfactant system in an amount of 0.1 to 50 wt-%, more preferably from 5 to 30 wt-%, and even more preferably from 10 to 25 wt-% with respect to the weight of the composition. There are few limitations on the type or the amount of the surfactants. In general, the surfactants may be chosen from the surfactants described in well-known textbooks like "Surface Active Agents" Vol. 1, by Schwartz & Perry, Interscience 1949, Vol. 2 by Schwartz, Perry & Berch, Interscience 1958, and/or the current edition of "McCutcheon's Emulsifiers and Detergents" published by Manufacturing Confectioners Company or in "Tenside-Taschenbuch", H. Stache, $2^{nd}$ Edn., Carl Hauser Verlag, 1981: "Handbook of Industrial Surfactants" ($4^{th}$ Edn.) by Michael Ash and Irene Ash; Synapse Information Resources, 2008. The type of surfactant selected may depend on the type of application for which the product is intended. The surfactant system may comprise one type of surfactant, or a mixture of two or more surfactants. Synthetic surfactants preferably form a major part of the surfactant system. Thus, the surfactant system preferably comprises one or more surfactants selected from one or more of anionic surfactants, cationic surfactants, non-ionic surfactants, amphoteric surfactants and zwitterionic surfactants. More preferably, the one or more detergent surfactants are anionic, nonionic, or a combination of anionic and nonionic surfactants. Mixtures of synthetic anionic and nonionic surfactants, or a wholly anionic mixed surfactant system or admixtures of anionic surfactants, nonionic surfactants and amphoteric or zwitterionic surfactants may all be used according to the choice of the formulator for the required cleaning duty and the required dose of the cleaning composition. Preferably, the surfactant system comprises one or more anionic surfactants. More preferably, the surfactant system comprises one or more anionic surfactants selected from the group consisting of lauryl ether sulfates and linear alkylbenzene sulphonates.

For certain applications the composition comprising a surfactant system preferably also comprises from 1 to 8 wt-% of an inorganic salt, preferably selected from sulfates and carbonates, more preferably selected from $MgSO_4$ and $Na_2SO_4$ and even more preferably $MgSO_4$. The composition comprising a surfactant system may be any product comprising surfactants. Preferably the composition comprising a surfactant system is a cleaning composition, more preferably a hand dish wash composition. In view of the favourable properties that the present method provides to the composition comprising the surfactant system, the composition preferably further comprises suspendable particles and/or air bubbles.

According to a nineteenth aspect, the invention also relates to a composition comprising a surfactant system wherein the composition also comprises the citrus fibre according to the invention and/or the composition of matter in dry form according to the invention. Herein, the surfactant system is as described above. The composition comprising a surfactant system preferably is a composition in dry form. Such a composition in dry form preferably comprises a composition of matter in dry form, wherein said composition of matter comprises citrus fibres and an additive distributed between said fibres. It is particularly preferred that the additive is sucrose and that the ratio A:F of additive to citrus fibre is 0.10 to 1.0 and 3.0 to 1.0 by weight.

Methods of Measurement

Sample Preparation: It is preferred that prior to any characterization, all citrus fibers' and compositions' samples made in accordance with the Examples and Comparative Experiments presented herein below, are milled using a Waring 8010EG laboratory blender (Waring Commercial, USA) equipped with a SS110 Pulverizer Stainless Steel Container using its low speed setting (18000 rpm) for 3 to 5 sec. The milled samples were sieved using a AS200 digital shaker from Retsch GmbH Germany with a sieve set of 10 mm, 500 μm, 250 μm and 50 μm sieves (50×200 mm), sieving conditions: 1 min at amplitude setting 60. Particles larger than 500 μm may be milled again until they pass sieve 500 μm.

Moistare content ("MC"): The moisture content was determined by weighing a milled sample placed in a pre-dried vessel and subsequently heating the vessel containing the sample overnight in an oven at 105° C. The moisture content (in wt %) was calculated as $(A_1-A_2)/A_1 \times 100$ where $A_1$ was the weight of the sample before drying in the oven and $A_2$ was the weight of the resulted dried sample, unless indicated otherwise.

Dry substance content ("DS") is measured according to formula:

$DS(\%) = 100\% - MC(\%)$

When the weight of anhydrous fibers in a composition needs to be determined, the above procedure can be utilized while correcting the moisture content for the additive content in the sample.

Standard deviation is computed according to the following formula:

$$\sqrt{\frac{\sum (x - \bar{x})^2}{(n-1)}}$$

where z is the sample mean average and n is the sample size.

$R_2^*$ measurements:

Sample preparation for NMR measurements: dispersions having fiber concentrations of 0.50 wt % were prepared by rehydrating milled and sieved samples in demineralized water. For each dispersion, an appropriate amount of sample (correcting for moisture and additive content) was weighed in 500 ml plastic pots and demineralized water was added to yield a total weight of 250 g. After subsequently adding 0.24 g of a preservative (Nipacide BIT20) and adjusting the pH to 3.6±0.1 using aqueous HCl, a further amount of demineralized water was added to yield a mixture with a total weight of 300 g. This mixture was homogenized at room temperature using a Silverson L4RT overhead batch mixer equipped with an Emulsor Screen (with round holes of about 1 mm diameter) operated for 2 min (120 sec.) at 3000 rpm. The mixtures were allowed to equilibrate overnight, after which the pH was standardized at 3.3±1 using concentrated HCl.

Calibration: an aliquot of the resulting pH-standardized mixture was transferred directly to a 18 cm flat bottom NMR tube of 10 mm diameter at a filling height of about 1 cm ensuring that upon placement of the sample in the NMR spectrometer, the fill height is within the region where the RF field of the coil of the NMR spectrometer is homogeneous. In order to do a background correction (calibration), another aliquot was centrifuged (Eppendorf Centrifuge 5416) for 10 min in a 2 ml Eppendorf cup at a relative centrifugation force of 15000 to separate the fibers from the liquid. The top layer (supernatant) of the centrifuged mixture without the fibre (hereinafter referred to as the "matrix reference sample") was transferred to a 18 cm flat bottom NMR tube at a filling height of 1 cm. Both the mixture and the matrix reference sample were incubated and equilibrated at 20° C. for 10 min. prior to the NMR measurement. The "relative centrifugal force", is defined as $r \times \omega^2/g$, where $g=9.8$ $ms^{-2}$ is the Earth's gravitational acceleration, r is the rotational radius of the centrifuge, $\omega$ is the angular velocity in radians per unit time. The angular velocity is $\omega = rpm \times 2\pi/60$, where rpm is the number of "revolutions per minute" of the centrifuge.

NMR measurement: Carr Purcell Meiboom Gill (CPMG) relaxation decay data were collected for each mixture and for each matrix reference sample. A Bruker MQ20 Minispec was used operating at a resonance frequency for protons of 20 MHz, equipped with a variable temperature probe-head stabilized at 20° C. Measurements were performed using a CPMG $T_2$ relaxation pulse sequence to observe the relaxation decay at 20° C. (See *Effects of diffusion on free precession in nuclear magnetic resonance experiments*, Carr, H. Y., Purcell, E. M., Physical Review, Volume 94, Issue 3, 1954, Pages 630-638/*Modified spin-echo method for measuring nuclear relaxation times*, Meiboom, S., Gill, D., Review of Scientific Instruments, Volume 29, Issue 8, 1958, Pages 688-691). Data were collected with the 180° pulse spacing set to 200 μs (microseconds), a recycle delay time of 30 sec, a 180°-pulse length of 5 μs and using 14.7 k 180°-pulses. The sequence deploys a phase cycle and complex mode detection.

Prior to measurement, the suitability of the NMR system for these measurements (in terms of field homogeneity etc.) was checked by verifying that the $T_2^*$ of pure water was >2 ms.

NMR data analysis ($R_2^*$ extraction): Data were processed with Matlab using a singular value decomposition to phase correct the quadrature data ("*Towards rapid and unique curve resolution of low-field NMR relaxation data: trilinear SLICING versus two-dimensional curve fitting*", Pedersen, H. T., Bro, R., Engelsen, S. B., *Journal of Magnetic Resonance. August* 2002; 157(1), Pages 141-155. DOI: 10.1006/jmre.2002.2570). The resulting, phase-corrected data were Inverse Laplace Transformed into a $T_2$ spectrum using the Matlab non-negative least square constraints function lsqnonneg (Lawson, C. L. and R. J. Hanson, *Solving Least Squares Problems*, Prentice-Hall, 1974, Chapter 23, p. 161) with boundaries set for $T_2$, requiring $T_2$ to be in the range of 0.01 to 10 seconds and with the regularization parameter lambda set to 0.2.

$R_2^*$ was determined as follows: from the $T_2$ distribution curve for a particular mixture, the peak corresponding to the water protons of which $T_2$ is averaged by exchange between the bulk water phase and the surface of the fiber material originating from the fiber mass was identified. Without being bound to any theory, the inventors believe that the exchange (and resulting averaging) is due to diffusion and chemical exchange between bulk and fibers' surface sites. The peaks of the bulk water phase are easily distinguished, as typically they are the peaks with the highest intensity. The peak corresponding to the bulk water phase in the matrix reference sample was similarly identified. The average $T_2$ value was determined by calculating the intensity-weighted average of the peak. $R_2$ is defined as the inverse of this average $T_2$, i.e. $R_2=1/T_2$ and is expressed in Hz. The $R_2^*$ for a given mixture is calculated as the difference between the $R_2$ of the mixture and $R_2$ of the matrix reference sample. Thus, $R_2^*$ is a measure for the bulk water interaction with the available fiber surface (K. R. Brownstein, C. E. Tarr, *Journal of Magnetic Resonance* (1969) Volume 26, Issue 1, April 1977, Pages 17-24). The characterization of the citrus fibers and compositions of the Examples and Comparative Experiments in terms of their $R_2^*$ is presented in Table 1c.

Rheology Measurements

Sample preparation for rheology measurements: dispersions were made by rehydrating in a buffer solution the milled and sieved samples. Dispersions with 0.2 wt % and 2.0 wt % fiber concentrations were prepared. The buffer solution was obtained by dissolving 40.824 grams of $KH_2PO_4$ in 2500 g of demineralized water using a magnetic stir bar. The pH of the buffer solution was raised to 7.0 by adding drops of 5M NaOH solution, after which demineralized water was added to obtain a total of 3000 gram of buffer solution. Each dispersion was prepared by weighing the appropriate amount of sample (correcting for moisture and if applicable additive content) in 500 ml plastic pots followed by addition of buffer solution to a total weight of 300 g. The sample was mixed with the buffer solution by mild stirring using a spoon. Subsequently, two different conditions were used to facilitate the dispersion. In one series of experiments, each dispersion was mixed with a Silverson L4RT overhead batch mixer equipped with an Emulsor Screen (with round holes of 1 mm diameter) for 2 min at 3000 rpm. In another series of experiments, each dispersion was treated with the same mixer for 10 min at 8000 rpm.

Measurments of G', YS and kinematic viscosity: the measurements were performed using an ARG2 rheometer from TA Instruments Ltd UK equipped with sand-blasted stainless steel parallel plates of 40 mm diameter and operated at a temperature of 20° C. using a measurement gap of 1.000 mm. To ensure that measurements are carried out on representative samples, the samples were gently stirred using a teaspoon just before placing an aliquot of the sample in the rheometer. The rheological analysis was carried out using a standard protocol including a time sweep, continuous ramps (up and down) of the shear rate and a strain sweep with the following settings:

Time sweep: delay 10 s, 5 min 0.1% strain at 1 Hz;

Continuous ramp step 1: 0.1 to 500 $s^{-1}$ shear rate duration 2 min; mode: log sampling: 10 point/decade;

Continuous ramp step 2: 500 to 0.1 $s^{-1}$ shear rate duration 2 min; mode: log sampling: 10 point/decade;

Strain sweep: Sweep: 0.1 to 500% Strain at 1 Hz, duration 2 min; mode: log sampling: 10 point/decade.

The data analysis software package form TA Instruments allowed extracting the storage modulus G', the kinematic viscosity and the yield stress (YS). G' is reported at the time of 300 seconds. The kinematic viscosity is reported at a shear rate of 22 $s^{-1}$ (down curve). The YS is determined from the maximum in the graph of G' versus strain %, and is defined as YS=G'×strain. The characterization of the citrus fibers and compositions of the Examples and Comparative Experiments in terms of G', viscosity and YS, are summarised in Tables 2 and 3.

Self-suspending capacity (SSC): 100 ml of a dispersion having 0.1 wt % fibre content was prepared as presented above in the "Rheology measurements" section. The dispersion was carefully poured to avoid air entrapping into a 100 ml graded glass measuring cylinder while keeping the cylinder slightly tilted. The top of the cylinder was closed using para-film. The closed cylinder was slowly shaken by tilting it ten times to mix and to remove any air bubbles that might be trapped in the dispersion. The cylinder was stored at room temperature and the fibers were allowed to settle under gravity. After 24 hours, SSC was determined by measuring the volume occupied by the fibers as determined by optical inspection and expressing it as a percentage from the total volume. Values are reported in Table 1. The higher the volume, the higher and thus better the SSC of the sample.

Viscosity ratio measurements indicating the ability of a fiber sample to develop its functionality on low shearing were made as follows: dispersions were prepared as presented above in the "Rheology measurements" section. A first viscosity was measured on the dispersions following the methodology presented in the "Rheology measurements". Subsequently, the dispersions were passed through a homogenizer at 250 bars and allowed to rest for about 1 hour at 20° C. to reach their equilibrium state. A second viscosity was measured under the same conditions as previously presented. The ratio of the first viscosity to the second viscosity is used as an indicator of the sample's capacity to reach functionality after low shear dispersion.

The invention will now be described with the help of the following examples and comparative experiments, without being however limited thereto.

Example 1

Dry citrus fibers were manufactured as follows:

Step (1) Water was added to de-pectinized citrus peel (a by-product of a pectin extraction process) to obtain an aqueous slurry having a dry substance content of about 4 wt %. The slurry was one time charged to a pressure homogenizer (APV homogenizer, Rannie 15-20.56) at 600 bars. An aqueous slurry containing citrus fibers was obtained.

Step (2) A precipitation tank was filled with an aqueous isopropanol solution (about 82 wt % isopropanol in water). The aqueous slurry containing citrus fibers was brought under agitation into the precipitation tank by using a volumetric pump and a precipitate in the form of granules having sizes between 5 mm and 50 mm was formed in the tank. The slurry:isopropanol ratio was 1:2. Agitation by stirring was provided while bringing said slurry into the tank and the precipitate was kept in the tank for about 30 minutes.

Step (3) The precipitate was charged to a centrifuge decanter (Flottweg centrifuge) operated at above 4000 rpm, to separate the liquid phase (i.e. water and isopropanol) from the citrus fibers.

Step (4) Steps (2) and (3) were repeated and the precipitate was subjected to an extraction step to increase the dry substance content. The extraction step was carried out by feeding the precipitate to a screw press. The speed and pressure of the press were adjusted to obtain a semi-dry cake having a dry substance content of about 22 wt %.

Step (5) The semi-dry cake was comminuted using a Lodige type FM 300 DMZ mixer, for about 15 to 30 minutes, to obtain grains having sizes in the range of 1 millimeter.

Step (6) The comminuted cake was dried in a ventilated oven at 40° C. for about 2 hours to reach a moisture content of about 8 wt %.

The properties of the obtained fibers are presented in Tables 1(a to c) to 3. FIG. 1 shows the $T_2$ distribution curves resulting from the inverse Laplace transform obtained during NMR data analysis for the sample of Example 1 and the corresponding matrix reference sample, respectively.

Examples 2 and 3

Dry compositions were manufactured as follows:
Example 1 was repeated with the difference that at step (5) the comminuted semi-dry cake was mixed with commercial sucrose in two sucrose:fiber ratios of 0.4:1 and 7:1, respectively. Before adding it, the commercial sucrose was milled to an average particle size of about 250 μm.

The properties of the obtained compositions are presented in Tables 1(a to c) to 3.

Figure 2:
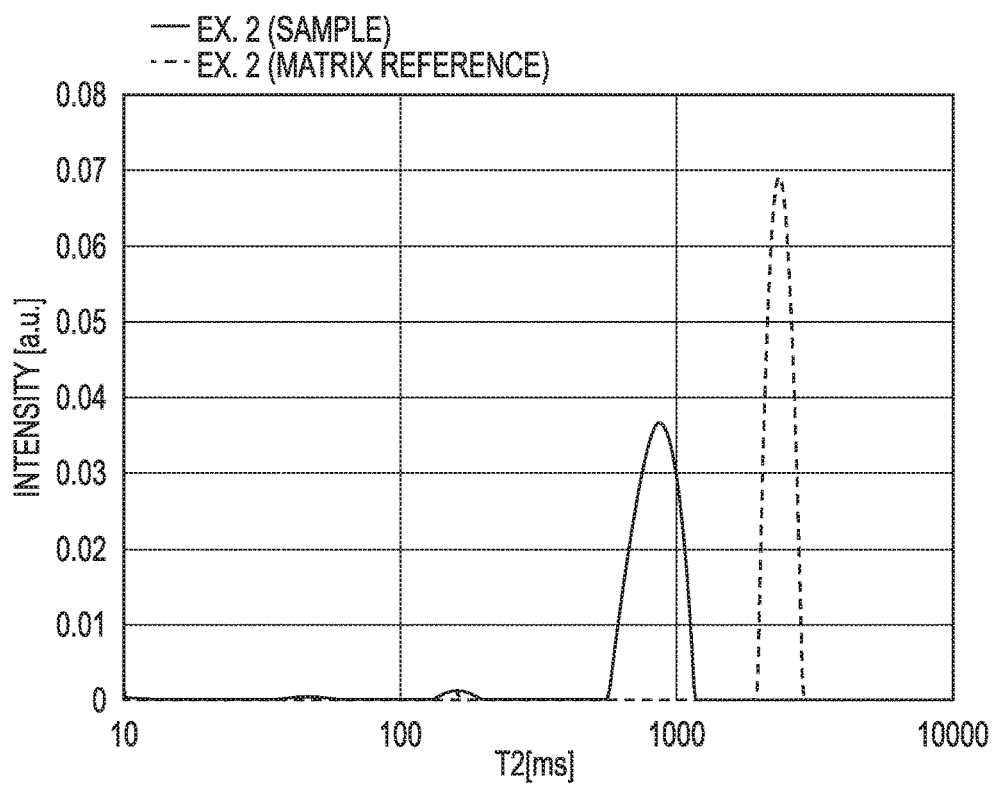

FIG. 2 shows the $T_2$ distribution curves resulting from the inverse Laplace transform obtained during NMR data analysis for the sample of Example 2 and the corresponding matrix reference sample, respectively.

Comparative Experiment 1

A dry composition was manufactured as follows:
Step (1) Water was added to de-pectinized citrus peel to obtain an aqueous slurry having a dry substance content of about 4 wt %. The slurry was charged to a pressure homogenizer (APV homogenizer, Rannie 15-20.56) at 600 bars. An aqueous slurry containing citrus fibers was obtained.

Step (2) The aqueous slurry containing citrus fibers was subjected to an extraction step with a screw press to increase the dry substance content to a level of about 22% wt %.

Step (3) The semi-dry cake was dried on an plate in an oven at 40° C. for several days to reach a moisture content of about 8 wt %.

The properties of the obtained fibers are presented in Tables 1(a to c) to 3.

Comparative Experiment 2 and 3

Example 1 of U.S. Pat. No. 6,485,767 was repeated. Commercial sucrose in two sucrose:fiber ratios of 0.1:1 and 5:1, respectively, was used as additive and added using a paddle mixer and mixed for 30 minutes. The sucrose had an average particles size of about 250 (?) μm.

The properties of the obtained fibers and compositions are presented in Tables 1(a to c) to 3. The comparative composition having a 5:1 sucrose:fiber ratio, cannot be prepared for measurements like the other samples due to increased stickiness and it was discarded.

Self-Suspending Capacity, $R_2^*$ and FAP Values

TABLE 1a

| | SSC (%) |
|---|---|
| Ex. 1 | 19 |
| Ex. 2 | 21 |
| Ex. 3 | 21 |
| CE. 1 | 3 |
| CE. 2 | 7 |
| CE. 3 | Not measurable |

TABLE 1b

| | FAP determination | | |
|---|---|---|---|
| | $R_2$(sample) (Hz) | $R_2$(matrix) (Hz) | FAP (Hz) |
| Ex. 1 | 0.79 | 0.41 | 0.37 |
| Ex. 2 | 1.16 | 0.42 | 0.74 |

As defined in the protocol above, the FAP parameter is determined on samples prepared and analyzed in the same way as described for the method of measurement for $R_2^*$, with the only difference being that during sample preparation, the mixtures containing the inventive fibers or compositions in water were homogenized at 1500 rpm. However, it was not possible to measure FAP on the samples made according to the comparative experiments, since these samples did not disperse well and/or did not stay in dispersion long enough to allow for the measurement to take place.

To enable the NMR characterization on the samples of comparative experiments, $R_2^*$ measurements were carried out on samples dispersed at 3000 rpm rather than 1500 rpm. The results are presented in Table 1c.

TABLE 1c

| | $R_2$* (Hz) dispersing at 3000 rpm |
|---|---|
| Ex. 1 | 1.242 |
| Ex. 2 | 1.23 |
| Ex. 3 | 0.949 |
| CE. 1 | 0.297 |
| CE. 2 | 0.626 |
| CE. 3 | Not measurable |

The fact that NMR measurements were only possible after dispersing the samples of the comparative experiments at higher rpms (thus higher shear) may be an indication of a larger available free-surface area for the fibers of the invention than that of known fibers.

Rheology Measurements

Samples of the above fibers and compositions were dispersed in water by stirring under the conditions mentioned in Tables 2 and 3 to obtain two fiber concentrations, i.e. 2 and 0.2 wt % of fibers in water, respectively. The rheology data are presented in said Tables 2 and 3.

It was observed that the inventive compositions have an optimal viscoelastic stability, e.g. fewer fluctuations of compositions' viscoelastic behavior. While the STDEV of the inventive compositions were systematically below 50% of MAX, those of the comparative experiments could not even be determined since the comparative sample having 5:1 sucrose:fiber ratio was not processable for the measurements. This is believed to demonstrate the ability of the inventive compositions to smoothen out viscoelastic fluctuations, which in turn may indicated a more reliable processing thereof.

It was also observed that the inventive compositions had greater $R_2$* values than the known compositions which was believed to indicate that the additive is optimally distributed between the citrus fibers and also between the microfibrils forming the citrus fibers. This in turn conferred to the inventive composition unique viscoelastic properties even at concentration of citrus fibers as low as 0.2 wt % thereby providing economy and ease of formulation, while still providing the necessary rheological behavior.

It was also observed that the inventive compositions had greater Fibre Availability Parameter (FAP) values than the known compositions which strengthened the belief that the additive is optimally distributed between the citrus fibers and also between the microfibrils forming the citrus fibers.

In particular it was observed that it may be possible to readily disperse the inventive composition by applying low levels of shear (e.g. 3000 rpm) and even lower, for short periods of time (e.g. 2 minutes) while providing homogeneity and stability of a wide variety of suspensions, such as those of the types used in foods, cosmetics, pharmaceuticals, but also those used in industrial products, such as paints and drilling muds.

From the presented data can also be observed that the fibers and compositions made in accordance with the invention were able to provide optimal rheological properties at extremely low concentrations e.g. 0.2 wt %. In contrast thereof, fibers and compositions prepared in accordance with the prior art failed to influence the rheological behavior of dispersions containing them at such low concentration.

Moreover, although readily dispersible at low shear levels, the fibers and compositions of the invention were extremely effective in providing optimum rheological properties to dispersions containing thereof also when dispersed under increased shear levels (e.g. 8000 rpm) for longer period of time (e.g. 10 min). Although herein called longer period of time, it is to be noted that 10 minutes is shorter than the time used in the prior art to disperse fibers.

Surprisingly, all of the above mentioned advantages were achieved with substantially chemically or enzymatically unmodified citrus fibers.

Example 4 and Comparative Example 4

Ready to drink tea beverages comprising citrus fibers, homogenized with different shear treatments were prepared using a method according to the invention and using a comparative method, respectively.

Citrus Fibers

For Example 4 (Ex. 4), the dry composition as described in Example 2, comprising citrus fibers and having a sucrose content of 28.6% (w/w) was used. Herbacel AQ+ citrus fibers were used in the comparative example (CE4).

Preparation of the Ready to Drink Milk Tea

Milk tea ingredients were combined with hot Millipore water of 90° C. as detailed in Table 4 to form 800 grams of ready-to-drink milk tea.

TABLE 4

| Ingredient | CE 4 (grams) | Ex. 4 (grams) |
|---|---|---|
| sucrose | 51.36 | 51.04 |
| creamer | 14.48 | 14.48 |
| Black tea powder | 2.15 | 2.15 |
| Herbacel AQ+ | 0.86 | |
| Composition of Ex 2 | | 1.20 |
| Water | balance | balance |

A mixer equipped with a small grid, 1 mm holes head during 5 minutes at 3000 rpm. Part of the milk tea compositions was used to determine particle size directly after the Silverson treatment (Ex. 4, and CE4, respectively) and another part was homogenized in a Gea Niro Soavi Panda Plus High Pressure Homogenizer in one pass at 250 bar (Ex 5 and CE5, respectively), as detailed in Table 5.

TABLE 5

| Shear treatment | CE4 | CE5 | Ex. 4 | Ex. 5 |
|---|---|---|---|---|
| Silverson | y | y | y | y |
| HPH 250 bar | | y | | y |

Particle Size Measurement

Particle size of the ready to drink milk tea samples (without any pretreatment such as e.g. sonication) was determined with a Malvern Mastersizer 2000 and expressed as d (0.1), d (0.5) and d (0.9) in table 6.

The value of d(0.5) is the diameter of the volume-equivalent sphere corresponding to the volume-weighted median particle volume (that is, half of the total volume of the dispersed material is made up of particles with a volume smaller than or equal to the median volume and half of the total volume of dispersed material has a larger volume). Correspondingly d(0.9) is the value where 90% of the total volume of the dispersed material is made up of particles with volumes smaller or equal to the volume of a sphere with this diameter and d(0.1) is the value where 10% of the total volume of the dispersed material is made up of particles with volumes smaller or equal to the volume of a sphere with this diameter

TABLE 6

|  | d (0.1) [μm] | d (0.5)) [μm] | d (0.9)) [μm] |
|---|---|---|---|
| CE 4 | 30.077 | 79.433 | 172.262 |
| CE 5 | 22.531 | 67.250 | 160.153 |
| Ex 4 | 0.176 | 23.975 | 87.929 |
| Ex 5 | 0.106 | 0.327 | 38.141 |

The difference in particle size between the Examples 4 and 5 according to the invention and the Comparative Examples CE4 and CE5 indicates that the physical stability of the products comprising the inventive composition of matter in dry form comprising citrus fibres and sucrose is higher than that of the comparative samples and that smaller particle sizes can be obtained with the inventive composition, even with the application of lower amounts of shear. Thus, these examples demonstrate that the method for preparing a composition comprising an aqueous phase comprising dispersed citrus fibres according the invention can be used to prepare an oil-in-water emulsion, such as an RTD milk tea with favourable properties, using a relatively limited amount of shear energy during product manufacture.

Examples 6 and 7 and Comparative Examples 6 and 7

Hand dishwash (HDW) surfactant formulations structured with different citrus fibre preparations were compared and investigated in terms of their rheological properties. Example 6 was structured with the dry citrus fibres of Example 1 above. Example 7 was structured with the composition of matter in dry form of Example 2 above, which contained 28.6% sucrose. Comparative example CE6 comprised non-defibrillated citrus fibre (Herbacel AQ+ type N, Herbafood, Germany). Comparative Example CE7 was prepared with Herbacel AQ+ type N citrus fibre material that was defibrillated using a high pressure homogeniser (Panda NS1001L, Niro-Soavi, Parma, Italy) operated at 200 bar. The preparation of the samples is discussed below. The formulations of the Example compositions 6, 7, CE6, and CE7 are provided in Table 7.

The rheology of the samples was analysed with a controlled stress rheometer (TA-AR 2000ex, TA instruments, Delaware, US) fitted with a sandblasted plate geometry (sandblasted plate diameter 40 mm, gap 1.5 mm) to obtain viscoelastic moduli (G') by a time sweep oscillation of 5 min at 20° C. with a strain of 0.1% and frequency of 1 Hz.

In addition, the ability to suspend particulates was investigated by stirring 1 wt % olive stone abrasive (16-30 mesh) into aliquots of each of the 4 samples, transferring these in 4 measured cylinders, and performing an accelerated stability test by storage of the samples in a temperature regulated cabinet at 45° C. At days 0, 3, and 5 the volume of the sedimented particles was recorded and expressed as % sediment by comparison to the total product volume. Results are presented in Table 9.

Preparation of Samples:

The hand dishwash compositions were made following the below preparation instructions:
1 Add demi-water in a beaker.
2 Add an equivalent of 0.25 wt % of citrus fibre material and hydrate with overhead paddle stirrer for 20 minutes (model RW27, IKA-Werke, Germany).
3. Add NaOH while mixing.
4. Add LAS acid while mixing.
5. Add SLES and mix until dissolved.
6. Add preservative while mixing.
7. Adjust pH1 between 6-7 using NaOH or citric acid.
8. For Examples 6 and 7, and comparative example CE6: Shear the whole formulation by single passage through an in-line Silverson at 8000 rpm using a flow of 300 ml/min.
9. For Comparative Example CE7: Shear the whole formulation by single passage through a high pressure homogeniser at 200 bar.
10. Add MgSO4.7H2O and mix until dissolved.

TABLE 7

Formulations of Ex 6, Ex7, CE6, and CE7.

| Ingredients | Ex 6 (% wt) | Ex 7 (% wt) | CE7, CE8 (% wt) |
|---|---|---|---|
| Demineralised water | 76.98 | 76.88 | 76.98 |
| Citrus Fibre of Ex. 1 | 0.25 | — | — |
| Citrus Fibre preparation of Ex. 2 | — | 0.35 | — |
| Herbacel AQ+ type N | — | — | 0.25 |
| NaOH (50%) | 3.23 | 3.23 | 3.23 |
| LAS acid (97%) | 11.60 | 11.60 | 11.60 |
| SLES 1EO (70%) | 5.36 | 5.36 | 5.36 |
| Nipacide BIT 20 preservative | 0.08 | 0.08 | 0.08 |
| MgSO4•7H2O | 2.50 | 2.50 | 2.50 |
| Total | 100.00 | 100.00 | 100.00 |

The results of the rheological measurements in Table 8 show that the HDW product of CE7, structured with reference material Herbacel AQ+ as treated above resulted in the lowest G' and yield stress values.

The use of pre-defibrillated citrus fibre material of Ex. 7 in a HDW formulation and further activation by an in-line Silverson mixer, significantly improved G' and yield stress of the HDW product.

The highest G' and yield stress value was obtained for the HDW product of Ex 7, structured with the citrus fibre preparation of Ex. 2. Stabilising the pre-defibrillated primary cell wall material used in Ex 7 with sucrose clearly further enhanced its structuring ability upon low shear activation.

Comparison shows that Example 6 exhibited a similar G' value as CE 7. However, Ex. 6 did not require high pressure homogenisation at 200 bar as CE7 did.

TABLE 8

G' (viscoelastic modulus) and yield stress of HDW products structured with citrus fibre material

|  | G' (Pa), n = 2 | SD* | Yield stress (Pa), n = 2 | SD* |
|---|---|---|---|---|
| CE 6 | 1.34 | ±0.01 | 0.03 | ±0.023 |
| Ex 6 | 5.64 | ±0.08 | 0.13 | ±0.001 |
| Ex 7 | 9.19 | ±0.23 | 0.24 | ±0.004 |
| CE 7 | 5.53 | ±0.51 | 0.06 | ±0.012 |

*SD = standard deviation

The accelerated suspension results of olive stones in the HDW products in Table 9 show that the suspending ability of the various samples followed the rheological behaviour of these samples as outlined in Table 8. The higher the G' and yield stress of the sample, the better its olive stone suspending properties. Ex. 7 provided the best suspension results.

TABLE 9

Accelerated suspension test at 45° C. of HDW products structured with citrus fibre material holding 1 wt % olive stone abrasive particles

| | Olive stone suspending ability of HDW products (ml ± SD) | | | |
|---|---|---|---|---|
| | day 0 | day 3 | day 5 | day 15 |
| CE 6 | 100 | 3.5 ± 0.7 | 3.2 ± 0.9 | 2.7 ± 0.5 |
| Ex 6 | 100 | 89.4 ± 0.2 | 81.2 ± 2.6 | 68.2 ± 2.1 |
| Ex 7 | 100 | 97.0 ± 0.1 | 89.1 ± 1.6 | 75.5 ± 0.1 |
| CE 7 | 100 | 82.6 ± 3.2 | 73.1 ± 0.2 | 60.3 ± 0.9 |

In conclusion, it was shown that citrus fibre material of the present invention only requires low shear activation to achieve similar or even superior product structure, whereas products structured with traditional citrus fibre—processed in the same way, or at higher shear activation—showed inferior structure.

TABLE 2

| Sample | | | | | Rheology 1 (2 minutes at 3000 rpm) | | | | | Rheology 2 (10 minutes at 8000 rpm) | | | | |
|---|---|---|---|---|---|---|---|---|---|---|---|---|---|---|
| | Sucrose:fiber ratio | Drying time (o) (min) | Moisture content (*) (%) | weight () (%) | Fiber conc. (*) (%) | G' (Pa) | σ(‡) of G' | % of MAX | YS (PA) | η at 22⁻¹ sec (Pa · s) | G' (Pa) | σ(‡) of G' | % of MAX | YS (PA) | η at 22⁻¹ sec (Pa · s) |
| Ex. 1 | 0:1 | 120 | 8 | 229 | 2 | 172 | 108 | 29 | 2.3 | 0.74 | 484.6 | 91 | 15 | 10.6 | 2.26 |
| Ex. 2 | 0.4:1 | 120 | | 290 | | 367(†) | | | 5.0 | 1.47 | 604.7(†) | | | 14.3 | 2.74 |
| Ex. 3 | 7:1 | 180 | | 1279 | | 191 | | | 3.1 | 0.82 | 426.8 | | | 8.8 | 1.85 |
| CE. 1 | 0:1 | 1440 | | 214 | | 0.11 | — | — | 0.04 | 0.004 | 17.95 | — | — | 0.2 | 0.10 |
| CE. 2 | 0.4:1 | 1440 | | 314 | | 2.59 | | | 0.4 | 0.02 | 155.7 | | | 1.5 | 0.60 |
| CE. 3 | 5:1 | 4320 | | 1256 | | N/M | | | N/M | N/M | N/M | | | N/M | N/M |

(o) = drying time to reach the mentioned moisture content.
(*) = moisture-s content of the dry composition.
(**) = sample's weight, i.e. the weight of the dispersed dry composition in water, used for rheological measurements.
(***) = citrus fiber's concentration in the dispersed dry composition in water.
(†) = MAX
(‡) = STDEV
N/M = not measurable

TABLE 3

| | Sucrose:fiber ratio | Drying time (o) (min) | Moisture content (*) (%) | Sample weight () (%) | Fiber conc. (*) (%) | Rheology 1 (2 minutes at 3000 rpm) | | | | | Rheology 2 (10 minutes at 8000 rpm) | | | | |
|---|---|---|---|---|---|---|---|---|---|---|---|---|---|---|---|
| | | | | | | G' (Pa) | σ(‡) of G' | % of MAX | YS (mPA) | η at 22⁻¹ sec (mPa · s) | G' (Pa) | σ(‡) of G' | % of MAX | YS (mPA) | η at 22⁻¹ sec (mPa · s) |
| Ex. 1 | 0:1 | 120 | 8 | 229 | 0.2 | 0.14 | 0.03 | 16 | 28 | 4.6 | 2.867 | 1.05 | 27 | 208 | 27.1 |
| Ex. 2 | 0.4:1 | 120 | | 290 | | 0.17 | | | 56 | 7.9 | 3.903(†) | | | 248 | 32.8 |
| Ex. 3 | 7:1 | 180 | | 1279 | | 0.20(†) | | | 40 | 5.1 | 1.809 | | | 241 | 22.3 |
| CE. 1 | 0:1 | 1440 | | 214 | | 0.01 | — | — | N/M | 1.9 | 0.068 | — | — | 10 | 2.8 |
| CE. 2 | 0.4:1 | 1440 | | 314 | | 0.07 | | | N/M | 2.3 | 0.0924 | | | 10 | 6.0 |
| CE. 3 | 5:1 | 4320 | | 1256 | | N/M | | | N/M | N/M | N/M | | | N/M | N/M |

(o) = drying time to reach the moisture content of 8%.
(*) = moisture content of the dry composition.
(**) = sample's weight, i.e. the weight of the dispersed dry composition in water, used for rheological measurements.
(***) = citrus fiber concentration of? the dispersed composition in water.
(†) = MAX
(‡) = STDEV
N/M = not measurable

The invention claimed is:

1. Citrus fibers in dry form, comprising a storage modulus (G') of at least 50 Pa, said G' being measured on an aqueous medium containing an amount of 2 wt % of the citrus fibers dispersed therein under a low-shear stirring of less than 10000 rpm, and an additive distributed between said fibers.

2. The citrus fibers of claim 1, said fibers having a transverse relaxation factor ("$R_2$") as measured by nuclear magnetic resonance ("NMR") of at least 0.35.

3. The citrus fibers of claim 1, said fibers having a self suspending capacity (SSC) of at least 5.

4. The citrus fibers of claim 1, said fibers having a yield stress (YS) of at least 2.0 Pa, said YS being measured on an aqueous medium containing an amount of 2 wt % citrus fibers dispersed therein under a low-shear stirring of less than 10000 rpm.

5. The citrus fibers of claim 1, wherein stirring is used to achieve the dispersion of the fibers in the aqueous medium and is at most 8000 rpm.

6. The citrus fibers of claim 1, wherein the additive is one or more polyols.

7. The citrus fibers of claim 1, the additive is chosen from the group consisting of glucose, sucrose, glycerol and sorbitol.

8. A composition of matter in dry form, comprising citrus fibers and an additive distributed between said fibers, said composition having a storage modulus (G') of at least 150 Pa, said G' being measured on an aqueous medium obtained by dispersing an amount of said composition therein under a low shear stirring of less than 10000 rpm to obtain a citrus fibers' concentration of 2 wt % relative to the total amount of the aqueous medium.

9. The composition of claim 8, containing an amount of water of at most 12 wt %.

10. The composition of claim 8, wherein the additive is one or more polyols.

11. The composition of claim 10, wherein the additive is chosen from the group consisting of glucose, sucrose, glycerol and sorbitol.

12. A method for manufacturing a composition comprising the steps of:
  a. homogenizing an aqueous slurry of a source of citrus fibers to obtain an aqueous slurry of citrus fibers;
  b. contacting the aqueous slurry of citrus fibers with an organic solvent to obtain a precipitate phase and a liquid phase; wherein the precipitate is in the form of granules;
  c. separating said precipitate phase from the liquid phase to obtain a semi-dry citrus fiber cake having a dry substance-content of at least 10 wt % relative to the mass of said cake;
  d. comminuting said cake to obtain grains containing citrus fibers and mixing said grains with an additive to obtain a semi-dry composition comprising citrus fibers and an additive; and
  e. subsequently desolventizing and/or dehydrating said semi-dry composition to obtain a dry composition containing citrus fibers and an additive and having a moisture content of preferably below 20 wt % relative to the total weight of the composition.

13. A food composition comprising the composition of claim 8, wherein said food composition is chosen from the group consisting of luxury drinks, milk component-containing drinks, nutrition-enriched drinks, dairy products, iced products, processed fat food products, soups, stews, seasonings, paste condiments, fillings, gels, paste-like food products, food products containing cereals as the main component, cakes, kneaded marine products, live-stock products, daily dishes, foods of delicate flavor, liquid diets, supplements and pet foods.

* * * * *